(12) United States Patent
Etkin et al.

(10) Patent No.: US 12,150,777 B2
(45) Date of Patent: Nov. 26, 2024

(54) TREATMENT OF DEPRESSION

(71) Applicants: The Board of Trustees of the Leland Stanford Junior University, Stanford, CA (US); Board of Regents, The University of Texas System, Austin, TX (US); The United States Government as Represented by the Department of Veterans Affairs, Washington, DC (US)

(72) Inventors: Amit Etkin, Palo Alto, CA (US); Yu Zhang, Palo Alto, CA (US); Greg Fonzo, Palo Alto, CA (US); Madhukar Trivedi, Palo Alto, CA (US)

(73) Assignees: THE BOARD OF TRUSTEES OF THE LELAND STANFORD JUNIOR UNIVERSITY, Stanford, CA (US); THE BOARD OF REGENTS, THE UNIVERSITY OF TEXAS SYSTEM, Austin, TX (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 925 days.

(21) Appl. No.: 16/981,822

(22) PCT Filed: Mar. 15, 2019

(86) PCT No.: PCT/US2019/022614
§ 371 (c)(1),
(2) Date: Sep. 17, 2020

(87) PCT Pub. No.: WO2019/182915
PCT Pub. Date: Sep. 26, 2019

(65) Prior Publication Data
US 2021/0038150 A1    Feb. 11, 2021

Related U.S. Application Data

(60) Provisional application No. 62/645,028, filed on Mar. 19, 2018.

(51) Int. Cl.
*A61B 5/16*      (2006.01)
*A61B 5/00*      (2006.01)
(Continued)

(52) U.S. Cl.
CPC .......... *A61B 5/4848* (2013.01); *A61B 5/0042* (2013.01); *A61B 5/0075* (2013.01);
(Continued)

(58) Field of Classification Search
CPC ... A61B 5/4848; A61B 5/0042; A61B 5/0075; A61B 5/055; A61B 5/165; A61B 5/316;
(Continued)

(56) References Cited

U.S. PATENT DOCUMENTS

2006/0129324 A1    6/2006   Rabinoff et al.
2006/0257903 A1   11/2006   Akil et al.
(Continued)

OTHER PUBLICATIONS

Shilyansky et al. (May 2016) "Effect of Antidepressant Treatment on Cognitive Impairments Associated with Depression: a Randomised Longitudinal Study", Lancet Psychiatry, 3(5):425-435.
(Continued)

*Primary Examiner* — Alexei Bykhovski
(74) *Attorney, Agent, or Firm* — Mintz, Levin, Cohn, Ferris, Glovsky and Popeo, P.C.

(57) ABSTRACT

Provided herein are, inter alia, methods for identifying subjects suffering from depression that will respond to treatment with an antidepressant.

15 Claims, 10 Drawing Sheets

(51) Int. Cl.
| | |
|---|---|
| A61B 5/055 | (2006.01) |
| A61B 5/316 | (2021.01) |
| A61B 5/369 | (2021.01) |
| G16H 10/20 | (2018.01) |
| G16H 20/70 | (2018.01) |
| G16H 50/20 | (2018.01) |
| A61K 31/135 | (2006.01) |

(52) U.S. Cl.
CPC .............. *A61B 5/055* (2013.01); *A61B 5/165* (2013.01); *A61B 5/316* (2021.01); *A61B 5/369* (2021.01); *A61B 5/7264* (2013.01); *A61B 5/7267* (2013.01); *G16H 10/20* (2018.01); *G16H 20/70* (2018.01); *G16H 50/20* (2018.01); *A61K 31/135* (2013.01)

(58) Field of Classification Search
CPC ..... A61B 5/369; A61B 5/7264; A61B 5/7267; A61B 5/4064; A61B 5/031; A61B 5/14553; G16H 10/20; G16H 20/70; G16H 50/20; A61K 31/135
See application file for complete search history.

(56) References Cited

U.S. PATENT DOCUMENTS

| | | | |
|---|---|---|---|
| 2010/0016751 A1 | 1/2010 | Hunter et al. | |
| 2012/0077818 A1* | 3/2012 | Campbell | A61P 25/04 514/252.19 |
| 2013/0102918 A1* | 4/2013 | Etkin | A61B 5/165 434/236 |
| 2013/0244990 A1 | 9/2013 | Schatzberg et al. | |
| 2018/0232486 A1* | 8/2018 | Carpenter | G06N 20/00 |
| 2018/0256912 A1* | 9/2018 | Leuchter | A61B 5/4836 |

OTHER PUBLICATIONS

Smith et al. (2004) "Advances in Functional and Structural MR Image Analysis and Implementation as FSL", Neuroimage, 23(Suppl 1):S208-S219.
Suzuki et al. (Nov. 1, 2015) "Transition from Reactive Control to Proactive Control Across Conflict Adaptation: An sLORETA Study", Brain and Cognition, 100:7-14.
Tabelow et al. (Oct. 31, 2011) "Statistical Parametric Maps for Functional MRI Experiments in R: The package Fmri", Journal of Statistical Software, 44:1-21.
Tang et al. (Jul. 1, 2013) "The Neural Oscillations of Conflict Adaptation in the Human Frontal Region", Biological Psychology, 93(3):364-372.
Tibshirani, Robert (1996) "Regression Shrinkage and Selection via the Lasso", Journal of the Royal Statistical Society, Series B, 58(1):267-288.
Tipping, Michaele (2001) "Sparse Bayesian Learning and the Relevance Vector Machine", Journal of Machine Learning Research, 1:211-244.
Trivedi et al. (Jul. 2016) "Establishing Moderators and Biosignatures of Antidepressant Response in Clinical Care (EMBARC): Rationale and Design", Journal of Psychiatric Research, 78:11-23.
Van Buuren et al. (Dec. 2011) "MICE: Multivariate Imputation by Chained Equations in R", Journal of Statistical Software, 45(3):1-67.
Voigt et al. (Oct. 2017) "Cost Effectiveness Analysis Comparing Repetitive Transcranial Magnetic Stimulation to Antidepressant Medications after a First Treatment Failure for Major Depressive Disorder in Newly Diagnosed Patients—A Lifetime Analysis", PLoS One, e0186950, 12(10):e0186950.
Wardenaar et al. (Aug. 30, 2010) "Development and Validation of a 30-Item Short Adaptation of the Mood and Anxiety Symptoms Questionnaire (MASQ)", Psychiatry Research, 179(1):101-106.
Williams et al. (Sep. 2015) "Amygdala Reactivity to Emotional Faces in the Prediction of General and Medication-Specific Responses to Antidepressant Treatment in the Randomized iSPOT-D Trial", Neuropsychopharmacology, 40:2398-2408.
Wipf et al. (Jul. 19, 2004) "Sparse Bayesian Learning for Basis Selection", IEEE Transactions on Signal processing, 52(8):2153-2164.
Xu et al. (Nov. 15, 2016) "Neural Systems Underlying Emotional and Non-emotional Interference Processing: An ALE Meta-Analysis of Functional Neuroimaging Studies", Frontiers in behavioral neuroscience, 10:220.
Xue et al. (Mar. 2017) "Abnormal Neural Basis of Emotional Conflict Control in Treatment-Resistant Depression: An Event-Related Potential Study", Clinical EEG and neuroscience, 48(2):103-110.
Zhang et al. (Sep. 23, 2015) "Sparse Bayesian Classification of EEG for Brain-Computer Interface", IEEE transactions on neural networks and learning systems, 27(11):2256-2267.
Behrens et al. (Jun. 15, 2003) "Non-invasive Mapping of Connections Between Human Thalamus and Cortex using Diffusion Imaging", Nature Neuroscience, 6(7):750-757.
Buckner et al. (Nov. 2011) "The Organization of the Human Cerebellum Estimated by Intrinsic Functional Connectivity", Journal of Neurophysiology, 106(5):2322-2345.
Cawley et al. (Oct. 1, 2006) "Gene Selection in Cancer Classification using Sparse Logistic Regression with Bayesian Regularization", Bioinformatic, 22(19):2348-2355.
Cawley et al. (Apr. 1, 2007) "Preventing Over-Fitting during Model Selection via Bayesian Regularisation of the Hyper-Parameters", Journal of Machine Learning Research, 8:841-861.
Chen et al. (Sep. 2013) "Hippocampal Network Connectivity and Activation Differentiates Post-Traumatic Stress Disorder From Generalized Anxiety Disorder", Neuropsychopharmacology, 38(10):1889-1898.
Choi et al. (Oct. 2012) "The Organization of the Human Striatum Estimated by Intrinsic Functional Connectivity", Journal of Neurophysiology, 108(8):2242-2263.
Cipriani et al. (Apr. 7, 2018) "Comparative Efficacy and Acceptability of 21 Antidepressant Drugs for the Acute Treatment of Adults with Major Depressive Disorder: A Systematic Review and Network Meta-analysis", Lancet, 391(10128):1357-1366.
Clayson et al. (Sep. 20, 2013) "Adaptation to Emotional Conflict: Evidence from a Novel Face Emotion Paradigm", PloS one, 8(9):e75776.
Drysdale et al. (Jan. 2017) "Resting-state Connectivity Biomarkers Define Neurophysiological Subtypes of Depression", Nature Medicine, 23(1):28-38.
Egner et al. (Jun. 1, 2008) "Dissociable Neural Systems Resolve Conflict from Emotional versus Nonemotional Distracters", Cerebral Cortex, 18(6):1475-1484.
Etkin et al. (May 2015) "A Cognitive-Emotional Biomarker for Predicting Remission With Antidepressant Medications: A Report From The Ispot-D Trial", Neuropsychopharmacology, 40(6):1332-1342.
Etkin et al. (2011) "Common Abnormalities and Disorder-Specific Compensation During Implicit Regulation of Emotional Processing in Generalized Anxiety and Major Depressive Disorders", The American journal of psychiatry, 168(9):968-978.
Etkin et al. (2010) "Failure of Anterior Cingulate Activation and Connectivity with the Amygdala During Implicit Regulation of Emotional Processing in Generalized Anxiety Disorder", The American Journal of Psychiatry, 167(5):545-554.
Etkin et al. (Sep. 21, 2006) "Resolving Emotional Conflict: A Role for the Rostral Anterior Cingulate Cortex in Modulating Activity in the Amygdala", Neuron, 51(6):871-882.
Etkin et al. (Nov. 2015) "The Neural Bases of Emotion Regulation", Nature Reviews Neuroscience, 6(11):693-700.
First et al. (1996) "Structured Clinical Interview for the DSM-IV-TR Axis I Disorders (SCID PTSD Module)", Research Version, Patient Edition.2002, New York: Biometrics Research, New York State Psychiatric Institute, 2 pages.
Fonzo et al. (Dec. 1, 2017) "PTSD Psychotherapy Outcome Predicted by Brain Activation During Emotional Reactivity and Regulation", American Journal of Psychiatry, 174(12):1163-1174.

(56) References Cited

OTHER PUBLICATIONS

Fonzo et al. (Dec. 1, 2017) "Selective Effects of Psychotherapy on Frontopolar Cortical Function in PTSD", American Journal of Psychiatry, 174(12):1175-1184.

Fournier et al. (Jan. 6, 2010) "Antidepressant Drug Effects and Depression Severity: A Patient-level Meta-analysis", JAMA, 303(1):47-53.

Friston et al. (1995) "Statistical Parametric Maps in Functional Imaging: A General Linear Approach", Human Brain Mapping, 2:189-210.

George et al. (May 2010) "Daily Left Prefrontal Transcranial Magnetic Stimulation Therapy for Major Depressive Disorder: a sham-controlled randomized trial", Archives of General Psychiatry, 67(5):507-516.

Gyurak et al. (Apr. 2011) "Explicit and Implicit Emotion Regulation: A Dualprocess Framework", Cognition and Emotion, 25(3):400-412.

Gyurak et al. (Feb. 15, 2016) "Frontoparietal Activation During Response Inhibition Predicts Remission to Antidepressants in Patients With Major Depression", Biological Psychiatry, 79(4):274-281.

Hamilton, M. (Feb. 1960) "A Rating Scale for Depression", Journal of neurology, neurosurgery, and psychiatry, 23(1):56-62.

Hasin et al. (Apr. 1, 2018) "Epidemiology of Adult DSM-5 Major Depressive Disorder and Its Specifiers in the United States", Jama Psychiatry, 75(4):336-346.

Insel et al. (May 1, 2015) "Brain disorders? Precisely", Science, 348(6234):499-500.

Jenkinson et al. (Aug. 15, 2012) "FSL", NeuroImage, 62(2):782-790.

Kerns et al. (Mar. 2004) "Anterior Cingulate Conflict Monitoring and Adjustments in Control", Science, 303(5660):1023-1026.

Khan et al. (Oct. 2015) "Antidepressants Versus Placebo in Major Depression: An Overview", World Psychiatry, 14(3):294-300.

Kirsch et al. (Feb. 26, 2008) "Initial Severity and Antidepressant Benefits: A Meta-Analysis of Data Submitted to the Food and Drug Administration", PLoS Medicine, e5, 5(2):9 pages.

Korb et al. (Jul. 2009) "Rostral Anterior Cingulate Cortex Theta Current Density and Response to Antidepressants and Placebo in Major Depression", Clinical Neurophysiology, 120(7):1313-1319.

Kraemer, Helena C. (Jul. 1, 2016) "Messages for Clinicians: Moderators and Mediators of Treatment Outcome in Randomized Clinical Trials", The American Journal of Psychiatry, 173(7):672-679.

Langenecker et al. (Dec. 1, 2007) "Frontal and Limbic Activation During Inhibitory Control Predicts Treatment Response in Major Depressive Disorder", Biological psychiatry, 62(11):1272-1280.

Larson et al. (Oct. 1, 2013) "Cognitive Conflict Adaptation in Generalized Anxiety Disorder", Biological Psychology, 94(2):408-418.

Li et al. (Oct. 2002) "Bayesian Automatic Relevance Determination Algorithms for Classifying Gene Expression Data", Bioinformatics, 18(10):1332-1339.

López-Muñoz et al. (May 1, 2009) "Monoaminergic Neurotransmission: the History of the Discovery of Antidepressants from 1950s Until Today", Current pharmaceutical design, 15(14):1563-1586.

Lynch et al. (May 20, 2004) "Activating Mutations in the Epidermal Growth Factor Receptor Underlying Responsiveness of Non-small-cell Lung Cancer to Gefitinib", The New England Journal of Medicine, 350(21):2129-2139.

Maier et al. (Oct. 1, 2012) "Impaired Conflict Adaptation in an Emotional Task Context following Rostral Anterior Cingulate Cortex Lesions in Humans", Journal of cognitive neuroscience, 24(10):2070-2079.

Marquand et al. (Sep. 1, 2016) "Beyond Lumping and Splitting: A Review of Computational Approaches for Stratifying Psychiatric Disorders", Biological psychiatry: cognitive neuroscience and neuroimaging, 1(5):433-447.

McLaren et al. (Jul. 16, 2012) "A Generalized Form of Context-Dependent Psychophysiological Interactions (gPPI): A Comparison to Standard Approaches", Neuroimage, 61:1277-1286.

Moore et al. (Feb. 1, 2017) "Adult Utilization of Psychiatric Drugs and Differences by Sex, Age, and Race", Jama internal medicine, 177(2):274-275.

Nguyen et al. (Jul. 2015) "Cost-Effectiveness of Repetitive Transcranial Magnetic Stimulation versus Antidepressant Therapy for Treatment-Resistant Depression", Value Health, 18(5):597-604.

O'Reardon et al. (Dec. 2007) "Efficacy and Safety of Transcranial Magnetic Stimulation in the Acute Treatment of Major Depression: A Multisite Randomized Controlled Trial", Biological Psychiatry, 62(11):1208-1216.

Paez et al. (Jun. 4, 2004) "EGFR Mutations in Lung Cancer: Correlation With Clinical Response to Gefitinib Therapy", Science, 304(5676):1497-1500.

Patenaude et al. (Jun. 1, 2011) "A Bayesian Model of Shape and Appearance for Subcortical Brain Segmentation", Neuroimage, 56(3):907-922.

Pescosolido et al. (Nov. 2010) ""A Disease Like Any Other"? A Decade of Change in Public Reactions to Schizophrenia, Depression, and Alcohol Dependence", American journal of psychiatry, 167(11):1321-1330.

Petty et al. (Jul. 10, 2017) "Gefitinib and EGFR Gene Copy Number Aberrations in Esophageal Cancer", Journal of Clinical Oncology, 35(20):2279-2287.

Pizzagalli, et al. (Jan. 26, 2018) "The Incremental Predictive Validity of Rostral Anterior Cingulate Cortex Activity in Relation to Symptom Improvement in Depression: A Randomized Clinical Trial", JAMA Psychiatry, 50 Pages.

Rush et al. (2003) "The 16-Item Quick Inventory of Depressive Symptomatology (QIDS), Clinician Rating (QIDS-C), and Self-Report (QIDS-SR): A Psychometric Evaluation in Patients with Chronic Major Depression", Society of Biological Psychiatry, 54:573-583.

Schaefer et al. (Sep. 2018) "Local-global Parcellation of the Human Cerebral Cortex from Intrinsic Functional Connectivity MRI", Cerebral Cortex, 28(9):3095-3114.

* cited by examiner

TREATMENT OF DEPRESSION

CROSS-REFERENCES TO RELATED APPLICATIONS

This application is a U.S. National Phase Application under 35 U.S.C. § 371 of PCT/US2019/022614, filed Mar. 15, 2019, which claims the benefit of U.S. Provisional Application No. 62/645,028, filed Mar. 19, 2018, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under U01MH092221 and U01MH092250 awarded by the National Institute of Mental Health of the National Institutes of Health. The government has certain rights in the invention.

BACKGROUND OF THE INVENTION

Major depression is a common, chronic and disabling medical condition, whose treatment mainstay over the past four decades has been monoaminergic antidepressant medications. As a result, roughly one in eight in the US takes antidepressants. Nonetheless, large meta-analyses have found only a small overall advantage of antidepressants over placebo when used in an unselected population of depressed patients, with clinical significance only in the most severe patients—a severity level the vast majority of depressed patients never reach. However, the clinical diagnosis of depression is composed of a heterogeneous mixture of biological phenotypes, which are not quantified in clinical trials or in clinical practice. As such, it may be that the small overall average superiority of antidepressants over placebo belies critical biological differences amongst depressed patients. That is, for some patients, antidepressants are far superior to placebo, while for others there is no benefit. Objective measures that can stratify depressed patients into those with clinically significant superiority of antidepressants over placebo, and those not seeing these benefits, are thus needed. Provided herein are solutions to this and other needs in the art.

BRIEF SUMMARY OF THE INVENTION

In an aspect is provided a method of identifying a subject suffering from depression that is likely to respond to treatment with an antidepressant, the method including: (a) administering a first incongruent trial followed by a second incongruent trial to the subject, and measuring a first brain activity level in a plurality of brain regions of the subject in response to the second incongruent trial, wherein the first and second incongruent trials form part of an emotional conflict task; (b) administering a congruent trial followed by a third incongruent trial to the subject, and measuring a second brain activity level in the plurality of brain regions of the subject in response to the third incongruent trial, wherein the congruent and third incongruent trials form part of the emotional conflict task; (c) quantifying a difference between the first brain activity level in each of the plurality of brain regions and the second brain activity level in each of the plurality of brain regions, respectively; and (d) identifying whether the subject will respond to treatment with an antidepressant by at least applying to each of the differences a machine learning model.

In an aspect is provided a method of detecting a brain activity level in a brain region of a subject suffering from depression, the method including: (a) administering a first incongruent trial followed by a second incongruent trial to the subject, and measuring a first brain activity level in a first brain region of the subject in response to the second incongruent trial, wherein the first and second incongruent trials form part of an emotional conflict task; (b) administering a congruent trial followed by a third incongruent trial to the subject, and measuring a second brain activity level in the first brain region of the subject in response to the third incongruent trial, wherein the congruent and third incongruent trials form part of the emotional conflict task; (c) quantifying a difference between the first brain activity level in the first brain region and the second brain activity level in the first brain region; and wherein the brain region is selected from the group consisting of a frontopolar cortex, a lateral prefrontal cortex, a dorsal anterior cingulate cortex, and an anterior insula.

BRIEF DESCRIPTION OF THE DRAWINGS

(FIG. 3A) Example congruent and incongruent stimuli. (FIG. 3B) Whole-brain significant moderation results. (FIGS. 3C-3E) Shown are: 1) the region of interest whose effects are shown (left-hand column); 2) its fMRI signal during conflict regulation comparing patients below and above the median of activity in that region, as well as healthy individuals for comparison (second column); 3) weekly depression severity (predicted $HAMD_{17}$ scores from the mixed models) for patients below and above the median of activity in that region; and 4) predicted remission rates for patients below and above the median of activity in that region, split by sertraline (SER) and placebo (PBO; third column). Regions shown here are: (FIG. 3C) left frontopolar cortex, (FIG. 3D) dorsal anterior cingulate, and (FIG. 3E) left anterior insula.

(FIG. 4B) Results of a median split are shown for the prominent rostral anterior cingulate cluster (FIG. 4A).

(FIG. 5A) A multivariate regression model trained on outcome with sertraline showed a strong correlation between predicted changes in $HAMD_{17}$ (for 10×10-fold cross-validation samples) and observed changes. (FIG. 5B) When applied to patients receiving placebo, the sertraline regression model failed to predict placebo outcome, illustrating its sertraline-specificity. (FIG. 5C) Regional weights (absolute value) contributing to the sertraline regression model, thresholded at weight=1.

DETAILED DESCRIPTION OF THE INVENTION

I. Definitions

Figure 1:
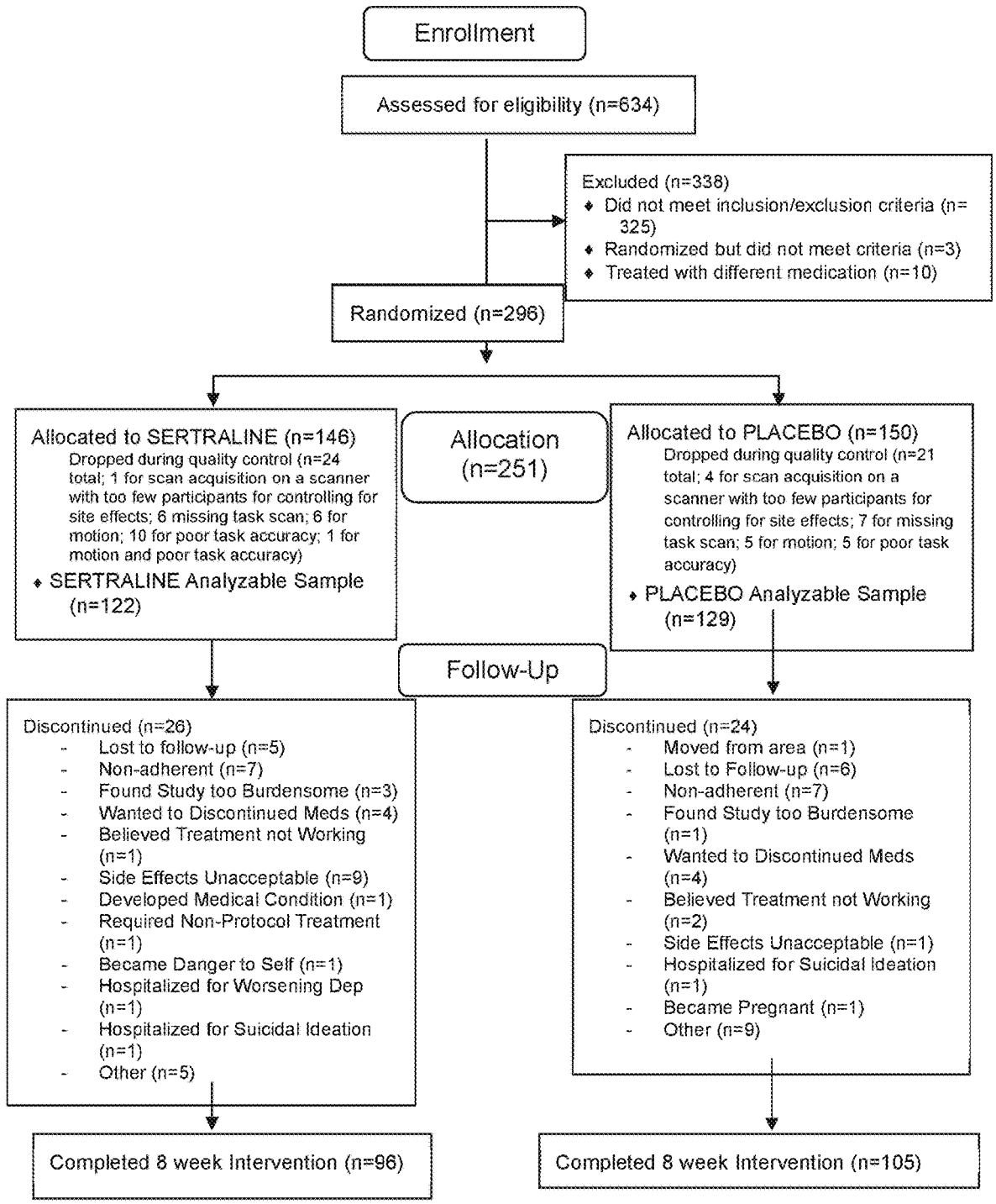
FIG. 1. EMBARC CONSORT Flow Diagram. For this analysis, patients were included (1) regardless of their $HAMD_{17}$ score, and (2) had emotional conflict task fMRI data of sufficient quality.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The term "brain region(s)" is used according to its plain and ordinary meaning and refers to a brain anatomical region following standard neuroanatomy hierarchies (e.g. a functional, connective or developmental region). Exemplary brain regions include, but are not limited to, brainstem, Medulla oblongata, Medullary pyramids, Olivary body, Inferior olivary nucleus, Rostral ventrolateral medulla, Respiratory center, Dorsal respiratory group, Ventral respiratory group, Pre-Botzinger complex, Botzinger complex, Paramedian reticular nucleus, Cuneate nucleus, Gracile nucleus, Intercalated nucleus, Area postrema, Medullary cranial nerve nuclei, Inferior salivatory nucleus, Nucleus ambiguus, Dorsal nucleus of vagus nerve, Hypoglossal nucleus, Solitary nucleus, Pons, Pontine nuclei, Pontine cranial nerve nuclei, chief or pontine nucleus of the trigeminal nerve sensory nucleus (V), Motor nucleus for the trigeminal nerve (V), Abducens nerve (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, Tectum, Corpora quadrigemina, inferior colliculi, superior colliculi, Pretectum, Tegmentum, Periaqueductal gray, Parabrachial area, Medial parabrachial nucleus, Lateral parabrachial nucleus, Subparabrachial nucleus (Kölliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), Pineal body, Habenular nucleim Stria medullares, Taenia thalami, Subcommissural organ, Thalamus, Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial geniculate body, Lateral geniculate body, Thalamic reticular nucleus, Hypothalamus, limbic system, HPA axis, preoptic area, Medial preoptic nucleus, Suprachiasmatic nucleus, Paraventricular nucleus, Supraoptic nucleusm Anterior hypothalamic nucleus, Lateral preoptic nucleus, median preoptic nucleus, periventricular preoptic nucleus, Tuberal, Dorsomedial hypothalamic nucleus, Ventromedial nucleus, Arcuate nucleus, Lateral area, Tuberal part of Lateral nucleus, Lateral tuberal nuclei, Mammillary nuclei, Posterior nucleus, Lateral area, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, Subthalamus, Subthalamic nucleus, Zona incerta, Pituitary gland, neurohypophysis, Pars intermedia, adenohypophysis, cerebral hemispheres, Corona radiata, Internal capsule, External capsule, Extreme capsule, Arcuate fasciculus, Uncinate fasciculus, Perforant Path, Hippocampus, Dentate gyrus, Cornu ammonis, Cornu ammonis area 1, Cornu ammonis area 2, Cornu ammonis area 3, Cornu ammonis area 4, Amygdala, Central nucleus, Medial nucleus (accessory olfactory system), Cortical and basomedial nuclei, Lateral and basolateral nuclei, extended amygdala, Stria terminalis, Bed nucleus of the stria terminalis, Claustrum, Basal ganglia, Striatum, Dorsal striatum (aka neostriatum), Putamen, Caudate nucleus, Ventral striatum, Striatum, Nucleus accumbens, Olfactory tubercle, Globus pallidus, Subthalamic nucleus, Basal forebrain, Anterior perforated substance, Substantia innominata, Nucleus basalis, Diagonal band of Broca, Septal nuclei, Medial septal nuclei, Lamina terminalis, Vascular organ of lamina terminalis, Olfactory bulb, Piriform cortex, Anterior olfactory nucleus, Olfactory tract, Anterior commissure, Uncus, Cerebral cortex, Frontal lobe, Frontal cortex, Primary motor cortex, Supplementary motor cortex, Premotor cortex, Prefrontal cortex, frontopolar cortex, Orbitofrontal cortex, Dorsolateral prefrontal cortex, dorsomedial prefrontal cortex, ventrolateral prefrontal cortex, lateral prefrontal cortex, Superior frontal gyms, Middle frontal gyms, Inferior frontal gyms, Brodmann areas: 4, 6, 8, 9, 10, 11, 12, 24, 25, 32, 33, 44, 45, 46, 47, Parietal lobe, Parietal cortex, Primary somatosensory cortex (S1), Secondary somatosensory cortex (S2), Posterior parietal cortex, postcentral gyms, precuneus, Brodmann areas 1, 2, 3 (Primary somesthetic area); 5, 7, 23, 26, 29, 31, 39, 40, Occipital lobe, Primary visual cortex (V1), V2, V3, V4, V5/MT, Lateral occipital gyms, Cuneus, Brodmann areas 17 (V1, primary visual cortex); 18, 19, temporal lobe, Primary auditory cortex (A1), secondary auditory cortex (A2), Inferior temporal cortex, Posterior inferior temporal cortex, Superior temporal gyms, Middle temporal gyms, Inferior temporal gyms, Entorhinal Cortex, Perirhinal Cortex, Parahippocampal gyms, Fusiform gyms, Brodmann areas: 9, 20, 21, 22, 27, 34, 35, 36, 37, 38, 41, 42, Medial superior temporal area (MST), insular cortex, anterior insula, cingulate cortex, Anterior cingulate, dorsal anterior cingulate cortex, Posterior cingulate, dorsal cingulate, Retrosplenial cortex, Indusium griseum, Subgenual area 25, Brodmann areas 23, 24; 26, 29, 30 (retrosplenial areas); 31, 32, cranial nerves (Olfactory (I), Optic (II), Oculomotor (III), Trochlear (IV), Trigeminal (V), Abducens (VI), Facial (VII), Vestibulocochlear (VIII), Glossopharyngeal (IX), Vagus (X), Accessory (XI), Hypoglossal (XII)), and neural pathways Superior longitudinal fasciculus, Arcuate fasciculus, Thalamocortical radiations, Cerebral peduncle, Corpus callosum, Posterior commissure, Pyramidal or corticospinal tract, Medial longitudinal fasciculus, dopamine system, Mesocortical pathway, Mesolimbic pathway, Nigrostriatal pathway, Tuberoinfundibular pathway, serotonin system, Norepinephrine Pathways, Posterior column-medial lemniscus pathway, Spinothalamic tract, Lateral spinothalamic tract, Anterior spinothalamic tract. Brain regions and specific parts of brain regions may be referred to according to their rostral/caudal, dorsal/ventral, medial/lateral, and/or anterior/posterior positions within the brain region with respect to the skull. In certain circumstances, brain regions may be generally referred to as cortical or subcortical brain regions depending on whether they form part of the cerebral cortex (e.g., part of the frontal, parietal, temporal, or occipital lobes) or are regions located below the cerebral cortex (e.g., basal ganglia, thalamus, internal capsule, brainstem, and cerebellum).

The term "brain region connectivity", "functional brain region connectivity", "brain circuit", "brain (or neural) connection", "brain network" or the like refers to a plurality of brain regions having neural activity (e.g., quantifiable brain activity levels) correlated with each other. For example, connectivity may be established where brain regions are active simultaneously, approximately simultaneous, or close in time (e.g. within a minute, an hour or three hours) in response to a stimulus or activity.

As used herein, the term "brain activity level" refers to measurable (e.g., quantifiable) neural activity. Measurable neural activity includes, but is not limited to, a magnitude of activity, a frequency of activity, a delay of activity, or a duration of activity. Brain activity levels may be measured (e.g., quantified) during periods in which no stimulus is presented. In embodiments, the brain activity level measured in the absence of a stimulus is referred to as a baseline brain activity level. Alternatively, brain activity levels may be measured (e.g., quantified) when one or more stimuli are delivered (e.g., an emotional conflict task). In embodiments, the brain activity level measured in the presence of a stimulus is referred to as a brain activity level response. Brain activity levels may be measured simultaneously or sequentially throughout the whole brain, or restricted to specific brain regions (e.g., frontopolar cortex, lateral prefrontal cortex, dorsal anterior cingulate, anterior insula). In embodiments, the brain activity level is determined relative to a baseline brain activity level taken during a baseline period. The baseline period is typically a period during which a stimulus is not presented or has not been presented for a sufficient amount of time (e.g., great than at least 0.05, 0.1, 0.15, 0.25, 0.5, 1, 2, 3, 4, 5, 10, 15, 30, 60 seconds or more).

A brain activity level may also encompass evaluating functional brain region connectivity. For example, neural activity recorded in a plurality of brain regions may have a specific time course across brain regions that can be correlated to reveal a functional brain connectivity pattern (e.g., at a first time point a first brain regions shows an increase in neural activity and at a second time point a second brain region shows an increase in activity). Methods for relating or correlating brain region activity levels across time to identify functional brain region connectivity may be found, for example, described in Example 3. Thus, in embodiments, a brain activity level is a measurement (e.g., quantification) of a time course of neural activity across a plurality of brain regions. In embodiments, a brain activity level is a sequence of brain region activity levels measured (e.g., quantified) across different brain regions over time. In embodiments, a brain activity level is a functional brain region connectivity pattern.

It is contemplated that any suitable method of measuring brain activity levels (e.g., neural activity) including, but not limited to, EEG, MEG, fMRI, and fNIRS may be used for practicing the methods described herein, including embodiments thereof.

In embodiments, a measured brain activity level is a magnitude of neural activity. In embodiments, a measured brain activity level is a magnitude of neural activity measured at 25-50 msecs, 100-150 msecs, or 180 and 200 msecs following delivery of a stimulus (e.g., emotional conflict task trial). The magnitude can be measured between 25-50 msecs (p30), 30-70 msecs (p60), 70-120 msecs (n100), 150-250 msecs (p200). Alternatively, the frequency of the brain activity level can be measured. In embodiments, the brain activity level may have a frequency of, for example, delta (0.5-4 Hz), theta (5-8 Hz), alpha (8-12 Hz), beta (12-30 Hz), or gamma (30-60 Hz). Similarly, the brain activity level can be measured by detecting the amplitude (e.g., power) of oscillations at delta (0.5-4 Hz), theta (5-8 Hz), alpha (8-12 Hz), beta (12-30 Hz), or gamma (30-60 Hz) frequencies. In embodiments, the brain activity level frequency, amplitude (e.g., power), and phase can be measured. In embodiments, a duration of the brain activity level is measured. In embodiments, a presence or absence of a brain activity level is measured. In embodiments, a brain activity level may be an average brain activity level. In embodiments, a brain activity level may be a median brain activity level.

In embodiments, a brain activity level is an electrical potential or magnetic field recorded from the nervous system, e.g. brain, of a human or other animal, following presentation of a stimulus (e.g., a trial in an emotional conflict task) that is distinct from spontaneous potentials or fields as detected by electroencephalography (EEG), magnetoencephalography (MEG), or other electrophysiological or neurophysiological recording methods. Such potentials and fields are useful for monitoring brain function in health and disease, and, as described herein, may be used for prognostic purposes. The recorded electrical potential or magnetic field is often presented with an amplitude, phase and/or frequency, including the amplitude or power of the response frequency, which generally indicates an intensity and/or pattern of the response.

As used herein, the term "electroencephalography (EEG)" refers to a non-invasive neurophysiological technique that uses an electronic monitoring device to measure and record electrical activity in the brain.

As used herein, the term "magnetoencephalography (MEG)" refers to a non-invasive neurophysiological technique that measures the magnetic fields generated by neuronal activity of the brain. The spatial distributions of the magnetic fields are analyzed to localize the sources of the activity within the brain.

Alternatively, in embodiments, a brain activity level is a blood flow (e.g., oxygenation level) or blood hemoglobin concentration change as recorded from the nervous system, e.g. brain, of a human or other animal, following presentation of a stimulus (e.g., a trial in an emotional conflict task), that is distinct from spontaneous blood flow (e.g., oxygenation level) or hemoglobin concentration changes as detected by functional magnetic resonance imaging (fMRI), functional near-infrared spectroscopy (fNIRS), or other suitable methods for detecting changes in blood flow (e.g., oxygenation level) or hemoglobin concentrations associated with changes in neural activity. Such changes are useful for diagnosis and monitoring of brain function in health and disease, and as described herein, may be used for prognostic purposes.

As used herein, the terms "functional magnetic resonance imaging (fMRI)" or "functional MRI (fMRI)" refer to a functional neuroimaging procedure using MRI technology that measures neural activity by detecting changes associated with blood flow.

As used herein, the term "functional near-infrared spectroscopy (fNIRS)" refers to a functional spectroscopic method that uses the near-infrared region of the electromagnetic spectrum (from about 700 nm to 2500 nm). For example, fNIRS can be used for non-invasive assessment of neural activity through the intact skull in human subjects by detecting changes in blood hemoglobin concentrations associated with neural activity.

It should be appreciated that brain activity levels measured in a subject may be compared to brain activity levels measured at a different time point (e.g., in response to different stimuli) in the same subject; to brain activity levels measured in a different subject, wherein the different subject suffers from the same psychiatric disorder (e.g., depression, major depression); or to a brain activity levels measured in a control subject (e.g., healthy control).

It is also contemplated that brain activity levels, as measured according to embodiments herein, may be classified (e.g., identified) as, for example, a brain activity level indicative of a subject being amendable to treatment (e.g., a depressed subject being responsive to treatment with an antidepressant). This type of classification (e.g., identification) may be useful, for example, to determine treatment outcome. Classification may be carried out by, for example, visual inspection and quantification performed by a human operator. Alternatively, classification may be accomplished via human operator-independent means. For example, classification may be accomplished through a computer running a machine learning model (e.g., algorithm) capable of classifying (e.g., identifying) a brain activity level indicative of a subject being amendable to treatment (e.g., a depressed subject being responsive to treatment with an antidepressant). The machine learning model may be any suitable machine learning model or algorithm known in the art. In embodiments, the model may be trained, for example using training data, to classify (e.g., identify) a subject being amendable to treatment (e.g., a depressed subject being responsive to treatment with an antidepressant). Training of the algorithm may be accomplished through supervised or unsupervised training methods.

A "subject" as used herein refers to an organism. In certain embodiments, the organism is an animal. In certain embodiments, the subject is a living organism. In certain embodiments, the subject is a cadaver organism. In certain embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient. In embodiments, the subject suffers from a psychiatric disorder. In embodiments, the subject suffers from depression. In embodiments, the subject has not been diagnosed with a psychiatric disorder. In embodiments, the subject is suspected of suffering from a psychiatric disorder. In embodiments, the psychiatric disorder is depression. In embodiments, the psychiatric disorder is major depression. In embodiments, the subject is suspected of suffering from depression. In embodiments, the subject suffers from depression. In embodiments, the subject is suspected of suffering from major depression. In embodiments, the subject suffers from major depression. In embodiments, the subject's primary diagnosis is depression. In embodiments, the subject's primary diagnosis is major depression. In embodiments, the subject does not have a lifetime history of psychosis. In embodiments, the subject does not suffer from posttraumatic stress disorder (PTSD). In embodiments, the subject does not suffer from bipolar disorder. In embodiments, the subject does not suffer from addiction or substance abuse. In embodiments, the subject does not have epilepsy. In embodiments, the subject does not have a comorbidity. In embodiments, the subject has a comorbidity. In embodiments, the comorbidity is anxiety. In embodiments, the comorbidity is social anxiety. In embodiments, the comorbidity is panic disorder. In embodiments, the comorbidity is generalized anxiety disorder (GAD). In embodiments, the comorbidity is not psychosis. In embodiments, the comorbidity is not PTSD. In embodiments, the comorbidity is not bipolar disorder. In embodiments, the comorbidity is not addiction or substance abuse. In embodiments, the comorbidity is not epilepsy.

The term "emotional conflict task" as used herein refers to the well-characterized paradigm that assesses emotional conflict and emotional conflict regulation. The emotional conflict task involves a series of trials (e.g., 5, 10, 15, 20, 30, 40, 50, 75, 100, 150, 200, 250, 300, or more trials) where each trial includes an emotional face overlaid with an emotion word. These trials are presented visually to the subject and the subject must identify the facial emotion. Identification may be performed, for example, via a key press. Trials may be "congruent trials," where the emotional face is overlaid with an emotion word that matches the emotional face or "incongruent trials," where the emotional face is overlaid with an emotion word that does not match the emotional face. For example, a congruent trial may have a face with a happy expression shown with the word "HAPPY" overlaid. An incongruent trial, on the other hand, may have a face with a happy expression shown with the word "FEAR" overlaid. Congruent and incongruent trials may be delivered randomly or pseudo-randomly, such that congruent trials may follow incongruent trials, congruent trials may follow congruent trials, incongruent trials may follow congruent trials, incongruent trials may follow incongruent trials, etc.

"Treating" or "treatment" as used herein (and as well-understood in the art) broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease or disorder (e.g., psychiatric disorder (e.g., depression, major depression)). Treatment may prevent the disease or disorder from occurring; relieve the disease's or disorder's symptoms (e.g., depression), fully or partially remove the disease's or disorder's underlying cause, shorten a disease's or disorder's duration, or do a combination of these things.

It is contemplated herein that treatment may occur through administration of administration of a medication. In embodiments, the medication is an antidepressant. In embodiments the antidepressant is a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, or an over-the-counter antidepressant.

The terms "selective serotonin reuptake inhibitor" or "SSRI" as used herein refer to a class of drugs that are typically used as antidepressants in the treatment of depression (e.g., depression, major depression) and anxiety disorders. The specific action of SSRIs is unknown but they are believed to increase the extracellular level of serotonin by limiting reuptake of serotonin. Non-limiting examples of SSRIs include citalopram, escitalopram, fluoxetine, fluvoxamine, paroxetine, and sertraline.

The terms "serotonin and norepinephrine reuptake inhibitor" or "SNRI" as used herein refer to a class of antidepressants used to treat depression (e.g., depression, major depression). SNRIs are monoamine reuptake inhibitors; that specifically inhibit reuptake of serotonin and norepinephrine. Non-limiting examples of SNRIs include desvenlafaxine, duloxetine, levomilnacipran, milnacipran, and venlafaxine.

The terms "monoamine oxidase inhibitor" or "MAOI" as used herein refer to a class of drugs used for treating depression (e.g., depression, major depression). Monoamine oxidase inhibitors inhibit the activity of one or both monoamine oxidase enzymes: monoamine oxidase A and monoamine oxidase B. Non-limiting examples of MAOIs include isocarboxazid, nialamide, phenelzine, hydracarbazine, tranylcypromirie, bifemelane, moclobemide, pirlindole, toloxatone, rasagiline, selegilin, caroxazone, and safinamide.

The terms "tricyclic antidepressant" or "TCA" as used herein refer to a class of medication used to primarily treat depression (e.g., depression, major depression). TCAs typically act by preventing the reuptake of serotonin and/or norepinephrine. Non-limiting examples of tricyclic antidepressants include amitriptyline, amitriptylinoxide, clomipramine, desipramine, dibenzepin, dimetacrine, dosulepin, doxepin, imipramine, lofepramine, melitracen, nitroxazepine, nortriptyline, noxiptiline, opipramol, pipofezine, protriptyline, and trimipramine.

The terms "serotonin modulator and stimulator" or "SMS" as used herein refer to a type of drug with a multimodal action specific to the serotonin neurotransmitter system. SM Ss may simultaneously modulate one or more serotonin receptors and inhibit the reuptake of serotonin. Non-limiting examples of SMSs include vilazodone and vortioxetine.

The terms "norepinephrine reuptake inhibitor" or "NRI" as used herein refer to a type of drug that acts as a reuptake inhibitor for the neurotransmitters norepinephrine (noradrenaline) and epinephrine (adrenaline) by blocking the action of the norepinephrine transporter (NET). Non-limiting examples of NRIs include reboxetine, teniloxazine, viloxazine, and atomoxetine.

The terms "norepinephrine-dopamine reuptake inhibitor" or "NDRI" as used herein refer to a type of drug that acts as a reuptake inhibitor for the neurotransmitters norepinephrine and dopamine by blocking the action of the norepinephrine transporter (NET) and the dopamine transporter (DAT), respectively. Non-limiting examples of NDRIs include bupropion, aminorntine, methylphenidate, and lisdexamfetamine.

The terms "serotonin antagonist and reuptake inhibitor" or "SARI" as used herein refer to a type of drug that acts to antagonize serotonin receptors such as $5\text{-HT}_{2A}$ and inhibit the reuptake of serotonin, norepinephrine, and/or dopamine. Some SARIs may additionally antagonize $\alpha_1$-adrenergic receptors. Non-limiting examples of SARIs include nefazodone and trazodone.

The terms "tetracyclic antidepressant" or "TeCA" as used herein refer to a class of antidepressants having a tetracyclic chemical structure. Non-limiting examples of TeCAs include amoxapine, maprotiline, mianserin, mirtazapine, and setiptiline.

The term "atypical antipsychotic" as used herein refers to a group of drugs used to treat psychiatric conditions including, but not limited to, bipolar disorder and depression (e.g., major depressive disorder). Non-limiting examples of atypical antipsychotics include amisulpride, lurasidone, and quetiapine.

The term "alternative antidepressant" as used herein refers to a group of drugs that do not fall under a class as described herein, but are useful for the treatment of depression. Non-limiting examples of alternative antidepressants include agomelatine, ketamine, tandospirone, tianeptine, and minocycline.

The term "over-the-counter antidepressant" as used herein refers to a group of drugs useful for the treatment of depression that can be obtained with a prescription or without. Non-limiting examples of over-the-counter antidepressants include ademetionine, *Hypericum perforatum*, oxitriptan, rubidium chloride, and tryptophan.

It is further contemplated that the types of antidepressants described herein may be used in combination with one another or with an adjunct. Non-limiting examples of combination treatments include amitriptyline/perphenazine, flupentixol/melitracen, olanzapine/fluoxetine, and tranylcypromine/trifluoperazine. Non-limiting examples of adjuncts include aripiprazole, brexpiprazole, lurasidone, olanzapine, quetiapine, risperidone, buspirone, lithium, yhyroxine (T4), and triiodothyronine (T3).

A complete list of antidepressants may be found in Lancet (2018) February 20. pii: S0140-6736(17)32802-7. doi: 10.1016/S0140-6736(17)32802-7, which is incorporated herein by reference in its entirety.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent. In embodiments, antidepressants are administered orally.

Administering may also be used in connection with an emotional conflict task. In these circumstances, administering refers to administering an emotional conflict task as described herein, including embodiments thereof, to a subject. In embodiments, the administration of the conflict task includes visual delivery of emotional conflict trials. In embodiments, visual delivery is accomplished via a screen or monitor.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease or disorder, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

To determine efficacy of treatment in psychiatric disorders (e.g., depression, major depression) questionnaires (e.g., self-reporting questionnaires) may be used. Non-limiting examples of questionnaires useful for assessing treatment efficacy in psychiatric disorders (e.g., depression, major depression) include the Hamilton Rating Scale for Depression; the Hamilton Rating Scale for Depression 17 item ($HAMD_{17}$ or HAMD-17); the 21 item HAMD ($HAMD_{21}$); the 24 item HAMD ($HAMD_{24}$); the Quick Inventory of Depressive Symptoms (QIDS); the Mood and Symptom Questionnaire subscale scores for Anxious Arousal, Anhedonic Depression, and General Distress; the Montgomery-Asberg Depression Scale (MADRS); the Beck Depression Inventory; the Clinical Global Impressions (GCI) scale); the Snaith-Hamilton Pleasure Scale (SHAPS). Questionnaires may be completed prior to, during, and following treatment, and changes in the scores may be used to determine treatment efficacy. In embodiments, the $HAMD_{17}$ is used to determine treatment efficacy. In embodiments, the HAMD is used to determine treatment efficacy. In embodiments, the $HAMD_{21}$ is used to determine treatment efficacy. In embodiments, the $HAMD_{24}$ is used to determine treatment efficacy. In embodiments, the QIDS is used to determine treatment efficacy. In embodiments, the Mood and Symptom Questionnaire subscale scores for Anxious Arousal, Anhedonic Depression, and General Distress is used to determine treatment efficacy. In embodiments, the MADRS is used to determine treatment efficacy. In embodiments, the Beck Depression Inventory is used to determine treatment efficacy. In embodiments, the GCI scale is used to determine treatment efficacy. In embodiments, treatment efficacy is determined by measuring (e.g., quantifying) a change in the $HAMD_{17}$ score. In embodiments, treatment efficacy is determined by measuring (e.g., quantifying) a change in the $HAMD_{21}$ score. In embodiments, treatment efficacy is determined by measuring (e.g., quantifying) a change in the HAMD score. In embodiments, treatment efficacy is determined by measuring (e.g., quantifying) a change in the $HAMD_{24}$ score. In embodiments, treatment efficacy is determined by measuring (e.g., quantifying) a change in the QIDS score. In embodiments, treatment efficacy is determined by measuring (e.g., quantifying) a change in the Mood and Symptom Questionnaire subscale scores for Anxious Arousal, Anhedonic Depression, and General Distress. In embodiments, treatment efficacy is determined by measuring (e.g., quantifying) a change in the MADRS score. In embodiments, treatment efficacy is determined by measuring (e.g., quantifying) a change in the Beck Depression Inventory score. In embodiments, treatment efficacy is determined by measuring (e.g., quantifying) a change in the GCI scale. In embodiments, treatment efficacy is determined by measuring (e.g., quantifying) a score on a questionnaire as described herein during a baseline period prior to treatment to a score on a questionnaire as described herein reported 1, 2, 3, 4, 6, 8 or more weeks after commencing treatment or terminating treatment.

Treatment may result in a reduction of symptoms (e.g., a response) or in remission. In embodiments, a reduction in symptoms is referred to as a response. In embodiments, a response is a 50% or greater decrease in symptoms. A response (e.g., a 50% or greater decrease in symptoms) to treatment may be determined by measuring (e.g., quantifying) a change in a score as described herein, including embodiments thereof, on a questionnaire as described herein, including embodiments thereof. In embodiments, remission is a score of 7 or less at endpoint on the $HAMD_{17}$. In embodiments, remission is a score of 7 or less at endpoint on the HAMD. In embodiments, remission is a score of 10 or less on the HAMD24. In embodiments, remission is a score of 5 or less on the QIDS. In embodiments, remission is a score of 9 or less on the MADRS.

II. METHODS

Provided herein are, inter alia, methods for determining whether a subject suffering from depression will respond to treatment with an antidepressant. Further, the methods provided herein are useful for determining whether a subject will benefit specifically from treatment with an antidepressant over a placebo.

In an aspect is provided a method of identifying a subject suffering from depression that is likely to respond to treatment with an antidepressant, the method including: (a) administering a first incongruent trial followed by a second incongruent trial to the subject, and measuring a first brain activity level in a plurality of brain regions of the subject in response to the second incongruent trial, wherein the first and second incongruent trials form part of an emotional conflict task; (b) administering a congruent trial followed by a third incongruent trial to the subject, and measuring a second brain activity level in the plurality of brain regions of the subject in response to the third incongruent trial, wherein the congruent and third incongruent trials form part of the emotional conflict task; (c) quantifying a difference between the first brain activity level in each of the plurality of brain regions and the second brain activity level in each of the plurality of brain regions, respectively; and (d) identifying whether the subject will respond to treatment with an antidepressant by at least applying to each of the differences a machine learning model. It should be appreciated that the use of first, second, and third to describe incongruent trials is merely for convention, and should not be construed to mean that specific, different incongruent trials are presented.

In embodiments, measuring a brain activity level means quantifying a brain activity level. In embodiments, quantifying means measuring. In embodiments, the difference is quantified by subtracting the second brain activity level from the first brain activity level.

In embodiments, the first brain activity level and the second brain activity level are measured via functional magnetic resonance imaging (fMRI), electroencephalography (EEG), functional near-infrared spectroscopy (fNIRS), or magnetoencephalography (MEG). In embodiments, the first brain activity level and the second brain activity level are measured via functional magnetic resonance imaging (fMRI). In embodiments, the first brain activity level and the second brain activity level are measured via EEG. In embodiments, the first brain activity level and the second brain activity level are measured via fNIRS. In embodiments, the first brain activity level and the second brain activity level are measured via MEG.

In embodiments, the antidepressant is a selective serotonin reuptake inhibitor (SSRI), a serotonin and norepinephrine reuptake inhibitor (SNRI), a serotonin modulator and stimulator (SMS), a serotonin antagnonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, or an over-the-counter antidepressant. In embodiments the antidepressant is a SSRI. In embodiments, the antidepressant is a SNRI. In embodiments, the antidepressant is a SMS. In embodiments, the antidepressant is a SARI. In embodiments, the antidepressant is a NRI. In embodiments, the antidepressant is a NDRI. In embodiments, the antidepressant is a MAOI. In embodiments, the antidepressant is a TeCA. In embodiments, the antidepressant is an atypical antipsychotic. In embodiments, the antidepressant is a TCA. In embodiments, the antidepressant is an alternative antidepressant. In embodiments, the antidepressant is an over-the-counter antidepressant.

In embodiments, the SSRI is sertraline. In embodiments, it is anticipated that the antidepressant will be delivered at an effective amount.

In embodiments, the machine learning model includes a neural network, a regression model, an instance-based model, a regularization model, a decision tree, a Bayesian model, a clustering model, an associative model, a deep learning model, a dimensionality reduction model, and/or an ensemble model. In embodiments, the machine learning model includes a neural network. In embodiments, the machine learning model includes a regression model. In embodiments, the machine learning model includes an instance-based model. In embodiments, the machine learning model includes a regularization model. In embodiments, the machine learning model includes a decision tree. In embodiments, the machine learning model includes a Bayesian model. In embodiments, the machine learning model includes a clustering model. In embodiments, the machine learning model includes an associative model. In embodiments, the machine learning model includes a deep learning model. In embodiments, the machine learning model includes a dimensionality reduction model. In embodiments, the machine learning model includes an ensemble model.

In embodiments, the Bayesian model is a Sparse Bayesian Learning model. The terms "Sparse Bayesian Learning model" or "SBL" as used herein refer to a machine learning technique that exploits an automatic relevance determination prior to penalizing unnecessary complexity in the model, such that it is able to automatically determine the feature sparsity under a Bayesian evidence framework. A description of Sparse Bayesian Learning can be found in Tipping M. E. (2001) Journal of Machine Learning Research 1:211-44 which is incorporated herein by reference in its entirety.

In embodiments, the machine learning model is trained to identify, based on the differences, whether the subject will respond to treatment with an antidepressant.

In embodiments, the method further includes training, based at least on training data, the machine learning model, the training data including a plurality of differences, and the machine learning model being trained to identify differences indicative of whether the subject will respond to treatment with an antidepressant. Methods for training a Sparse Bayesian Learning model may be found, for example, described in Example 2.

In embodiments, the training of a machine learning model is supervised. In this case, the training data used for training the model is linked to a known outcome (e.g., efficacy of treatment with an antidepressant). For example, the training data includes data (e.g., differences in first and second brain activity levels measured in one or a plurality of brain regions as described herein, including embodiments thereof) linked to a subject with a known outcome in response to antidepressant treatment. In embodiments, the outcome is determined by questionnaire scores. In embodiments, the outcome is determined by taking a difference between the questionnaire score prior to treatment and the questionnaire score during or following treatment. In embodiments, the questionnaire is a $HAMD_{17}$ questionnaire. Thus, the model may be trained to identify, based on differences in first and second brain activity levels in one or a plurality of brain regions, whether a subject will respond to treatment with an antidepressant. In this way, the model, when presented with new data (e.g., differences in first and second brain activity levels measured in one or a plurality of brain regions as described herein, including embodiments thereof) from a subject with an unknown outcome (i.e., prior to treatment), can identify whether the subject will respond to treatment with an antidepressant.

In embodiments, the training data includes a plurality of quantified first and second brain activity level differences in a plurality of brain regions associated with a treatment outcome, for example, determined by measuring changes in scores in a questionnaire as described herein, including embodiments thereof.

It should be appreciated that the machine learning model may be trained on data (e.g., differences in first and second brain activity levels measured in one or a plurality of brain regions as described herein, including embodiments thereof) obtained from subjects treated with a placebo and known outcomes determined by measuring changes in scores in a self-reporting questionnaire as described herein, including embodiments thereof.

In an aspect is provided a method of detecting a brain activity level in a brain region of a subject suffering from depression, the method including: (a) administering a first incongruent trial followed by a second incongruent trial to the subject, and measuring a first brain activity level in a first brain region of the subject in response to the second incongruent trial, wherein the first and second incongruent trials form part of an emotional conflict task; (b) administering a congruent trial followed by a third incongruent trial to the subject, and measuring a second brain activity level in the first brain region of the subject in response to the third incongruent trial, wherein the congruent and third incongruent trials form part of the emotional conflict task; (c) quantifying a difference between the first brain activity level in the first brain region and the second brain activity level in the first brain region; and wherein the brain region is selected from the group consisting of a frontopolar cortex, a lateral prefrontal cortex, a dorsal anterior cingulate cortex, and an anterior insula. In embodiments, the first brain region is a frontopolar cortex. In embodiments, the first brain region is a lateral prefrontal cortex. In embodiments, the first brain region is a dorsal anterior cingulate cortex. In embodiments, the first brain region is an anterior insula. As described supra, the use of first, second, and third to describe incongruent trials is merely for convention, and should not be construed to mean that specific, different incongruent trials are presented.

In embodiments, measuring a brain activity level means quantifying a brain activity level. In embodiments, quantifying means measuring. In embodiments, the difference is quantified by subtracting the second brain activity level from the first brain activity level.

In embodiments, steps (a), (b), and (c) are performed in a second brain region, a third brain region, and a fourth brain region, wherein each of the first brain region, the second brain region, the third brain region, and the fourth brain region is different. In embodiments, the second brain region is a frontopolar cortex. In embodiments, the second brain region is a lateral prefrontal cortex. In embodiments, the second brain region is a dorsal anterior cingulate cortex.

In embodiments, the second brain region is an anterior insula. In embodiments, the third brain region is a frontopolar cortex. In embodiments, the third brain region is a lateral prefrontal cortex. In embodiments, the third brain region is a dorsal anterior cingulate cortex. In embodiments, the third brain region is an anterior insula. In embodiments, the fourth brain region is a frontopolar cortex. In embodiments, the fourth brain region is a lateral prefrontal cortex. In embodiments, the fourth brain region is a dorsal anterior cingulate cortex. In embodiments, the fourth brain region is an anterior insula.

In embodiments, the first, second, third, and fourth brain regions are not a brain region other than a frontopolar cortex, a lateral prefrontal cortex, a dorsal anterior cingulate cortex, or an anterior insula.

In embodiments, the brain activity level in the brain region of the subject is not measured during a task that is not an emotional conflict task.

In embodiments, the subject does not suffer from a comorbidity.

In embodiments, the first brain activity level and the second brain activity are measured via fMRI, EEG, fNIRS, or MEG. In embodiments, the first brain activity level and the second brain activity are measured via fMRI. In embodiments, the first brain activity level and the second brain activity are measured via EEG. In embodiments, the first brain activity level and the second brain activity are measured via fNIRS. In embodiments, the first brain activity level and the second brain activity are measured via MEG.

In embodiments, the method further includes determining whether the subject is an antidepressant responsive subject, wherein the second brain activity level in the brain region of the subject being greater than the first brain activity level in the brain region of the subject is indicative of the subject being an antidepressant responsive subject. In embodiments, the suppression of brain activity level, indicated by a negative value if the second brain activity level is subtracted from the first brain activity level, in the brain region is indicative of the subject being an antidepressant responsive subject.

In embodiments, the antidepressant is a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, or an over-the-counter antidepressant. In embodiments, the antidepressant is a SSRI. In embodiments, the antidepressant is a SNRI. In embodiments, the antidepressant is a SMS. In embodiments, the antidepressant is a SARI. In embodiments, the antidepressant is a NRI. In embodiments, the antidepressant is a NDRI. In embodiments, the antidepressant is a MAOI. In embodiments, the antidepressant is a TeCA. In embodiments, the antidepressant is an atypical antipsychotic. In embodiments, the antidepressant is a TCA. In embodiments, the antidepressant is an alternative antidepressant. In embodiments, the antidepressant is an over-the-counter antidepressant.

In embodiments, the SSRI is sertraline. In embodiments, it is anticipated that the antidepressant will be delivered at an effective amount

III. EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1

Identification of Predictors of Antidepressant Treatment Using an Emotional Conflict Task Though a mainstay of depression treatment for decades, antidepressant medications are only modestly superior to placebo on average. This has led to substantial controversy regarding the efficacy and widespread use of these medications. Depression, however, is a biologically heterogeneous diagnosis and it may be that the small average superiority of antidepressants arises from large and identifiable treatment-relevant individual biological differences between patients. Here we tested whether brain activation during the regulation of emotional conflict, an adaptive mental capacity of direct relevance to depression, moderated between response to an antidepressant versus placebo.

Methods: We analyzed emotional conflict task functional neuroimaging data from the Establishing Moderators and Biosignatures of Antidepressant Response in Clinic Care (EMBARC) study, in which 309 non-medicated depressed outpatients were imaged prior to and one week into eight weeks of treatment with either sertraline or placebo. Imaging analyses were conducted within an intent-to-treat framework using whole-brain voxelwise correction for multiple comparisons. Results: Greater pretreatment capacity to regulate emotional conflict, evident in terms of greater regulation-related dampening of conflict-responsive activity in regions including the lateral prefrontal cortex and dorsal anterior cingulate, predicted improved outcome with sertraline versus placebo. Patients in the top quartile of emotional conflict regulatory ability remitted at a high rate (number needed to treat <4 versus placebo), while those in the bottom quartile saw no benefit of sertraline over placebo. Emotion conflict regulation was furthermore independent of clinical severity. Conclusions: Our findings demonstrate that antidepressant outcome is strongly moderated by a key self-regulatory capacity, which was objectively quantifiable using neuroimaging. Those patients with more robust emotional conflict regulation saw the greatest placebo-controlled benefit of sertraline. These findings thus provide strong evidence that a clinically and mechanistically meaningful stratification is possible in depression, and establish a path for greater personalization of treatment for this condition.

These findings allow us to objectively stratify depressed patients based on whether they are likely to see benefit with an antidepressant over placebo. Those identified as medication responders can be expected to have a high remission rate, and thus should be given the antidepressant. Those predicted to not respond differently from placebo may be better off exploring alternative interventions (repetitive transcranial magnetic stimulation, psychotherapy, electroconvulsive therapy). Additionally, this marker may be particularly helpful for participant selection in studies (e.g. when testing an agent to enrich for likely medication non-responders, or only take likely medication responders, in whom the effect of medication vs placebo is expected to be large).

Major depression is a common, chronic and disabling medical condition, whose treatment mainstay over the past four decades has been monoaminergic antidepressant medications. There are now many such medications approved by the United States Food and Drug Administration (FDA), and as a result roughly one in eight in the US takes antidepressants. Despite this apparent success, substantial controversy exists as to whether antidepressant medication is in fact superior to placebo. Large meta-analyses have found a small overall advantage of antidepressants (Cohen's d~0.3), with clinical significance evident only in the most severe patients—which is a severity level the vast majority of depressed patients never reach. However, the clinical diagnosis of depression is composed of a heterogeneous mixture of biological phenotypes, which are not quantified in clinical trials or clinical practice. As such, it may be that the small average overall superiority of antidepressants over placebo belies critical individual differences amongst depressed patients. That is, that for some patients, antidepressants are far superior to placebo, while for others there is no benefit (or antidepressants might even worsen their clinical state). Objective measures that can stratify depressed patients into those with clinically significant superiority of antidepressants over placebo and those not seeing these benefits are termed moderators. Here, we identify whether such treatment moderators exist, using objective neurobiological measures derived from an understanding of neural processes relevant for depression.

Though a mainstay of depression treatment for decades, antidepressant medications are only modestly superior to placebo on average. This has led to substantial controversy regarding the efficacy and widespread use of these medications. Depression, however, is a biologically heterogeneous diagnosis and it may be that the small average superiority of antidepressants arises from large and identifiable treatment-relevant individual biological differences between patients. Here we tested whether brain activation during the regulation of emotional conflict, an adaptive mental capacity of direct relevance to depression, moderated between response to an antidepressant versus placebo. Methods: We analyzed emotional conflict task functional neuroimaging data from the Establishing Moderators and Biosignatures of Antidepressant Response in Clinic Care (EMBARC) study, in which 309 non-medicated depressed outpatients were imaged prior to and one week into eight weeks of treatment with either sertraline or placebo. Imaging analyses were conducted within an intent-to-treat framework using whole-brain voxelwise correction for multiple comparisons. Results: Greater pretreatment capacity to regulate emotional conflict, evident in terms of greater regulation-related dampening of conflict-responsive activity in regions including the lateral prefrontal cortex and dorsal anterior cingulate, predicted improved outcome with sertraline versus placebo. Patients in the top quartile of emotional conflict regulatory ability remitted at a high rate (number needed to treat <4 versus placebo), while those in the bottom quartile saw no benefit of sertraline over placebo. Emotion conflict regulation was furthermore independent of clinical severity. Conclusions: Our findings demonstrate that antidepressant outcome is strongly moderated by a key self-regulatory capacity, which was objectively quantifiable using neuroimaging. Those patients with more robust emotional conflict regulation saw the greatest placebo-controlled benefit of sertraline.

Example 2

Brain Regulation of Emotional Conflict Moderates Antidepressant Treatment Outcome Abstract: Antidepressants are, on average, only modestly superior to placebo, primarily due to response heterogeneity and the lack of biological markers that could precisely match patients with treatments. Identification of specific markers to address disease and response heterogeneity could lead to precision in treatment selection and reduce unnecessary treatment trials. We tested whether brain activation during the regulation of emotional conflict, an adaptive mental capacity of direct relevance to depression, moderated subsequent treatment-specific responses to an antidepressant versus placebo. Neuroimaging was conducted prior to treatment initiation as part of the Establishing Moderators and Biosignatures of Antidepressant Response in Clinic Care (EMBARC) study, which randomized 309 non-medicated depressed outpatients to eight weeks of either sertraline or placebo treatment. Imaging analyses maintained an intent-to-treat framework with rigorous statistical analysis and correction for multiple comparisons. Brain activation robustly moderated the treatment effect. Greater pretreatment regulation-related dampening of prefrontal conflict-responsiveness (independent of clinical severity) predicted significantly better outcome with sertraline versus placebo. Patients in the top half of this emotion-regulation capacity remitted at a high rate (number needed to treat <5), while those in the bottom half saw no benefit of sertraline over placebo. Task-related activation also yielded a predictive multivariate regression model that was specific to sertraline response over placebo. Our findings demonstrate that antidepressant outcome is strongly moderated by a key self-regulatory capacity, which was objectively quantifiable using neuroimaging. Thus, a clinically and mechanistically meaningful stratification is now possible in depression, thereby establishing a path for better treatment personalization. Establishing Moderators and Biosignatures of Antidepressant Response for Clinical Care for Depression (EMBARC), NCT#01407094.

Major depression is a common, chronic and disabling medical condition[1], whose treatment mainstay over the past four decades has been monoaminergic antidepressant medications[2]. As a result, roughly one in eight in the US takes antidepressants[3]. Nonetheless, large meta-analyses have found only a small overall advantage of antidepressants over placebo (Cohen's d~0.3) when used in an unselected population of depressed patients, with clinical significance only in the most severe patients[4, 5-8]—a severity level the vast majority of depressed patients never reach[1]. Moreover, the clinical diagnosis of depression is composed of a heterogeneous mixture of biological phenotypes[9], which are not quantified in clinical trials or in clinical practice. As such, it may be that the small overall average superiority of antidepressants over placebo belies critical biological differences amongst depressed patients. Put differently, it may be that for some patients, antidepressants are far superior to placebo, while for others there is no benefit. Objective measures that can stratify for which depressed patients clinically significant superiority of antidepressants over placebo will be observed are termed moderators[10]. Here, our goal is therefore to identify whether such treatment moderators exist, using a well-established objective neurobiological measures derived from an understanding of neural processes relevant for depression.

The ability to regulate the brain response to conflicting emotional cues is a critical component of wellbeing[11-13], and is impaired in depression[14, 15]. Emotional conflict engages cognitive and emotion-related brain circuitry, including the lateral prefrontal cortices, anterior cingulate, insula and amygdala[16-18]. Conflict can be regulated dynamically across successive emotional conflict trials[11,17,18], a process that engages the rostral anterior cingulate and results in dampening of activity in the conflict-responsive regions noted above[17-19]. Patients with depression are impaired in their ability to regulate conflict-related brain activity[14,15]. Data from recent antidepressant treatment prediction studies, albeit all of which lacked a placebo control, have highlighted the importance of better cognitive functioning and prefrontal activation, along with decreased amygdala response to emotional cues, in predicting better treatment outcome[20-23]. It may be possible that the more intact an individual's ability to regulate emotional conflict—independent of clinical symptom severity—the greater their response to antidepressant treatment, compared to placebo. More generally, given the paucity of large placebo-controlled neuroimaging studies of antidepressant treatment, identification of any brain signature as a robust moderator would help ground our understanding of a key treatment-predictive depression phenotype in a well-studied affective neuroscience mechanistic framework.

We examined functional magnetic resonance imaging (fMRI) data on a previously-characterized emotional conflict task[17,18] as part of the Establishing Moderators and Biosignatures of Antidepressant Response in Clinic Care (EMBARC) study[24]. EMBARC is the largest neuroimaging-coupled placebo-controlled randomized clinical trial (RCT) in depression to date, and involved randomization of 309 medication-free depressed outpatients to receive either the selective serotonin reuptake inhibitor (SSRI) sertraline or placebo for eight weeks (FIG. 1). Analysis of pre-treatment neuroimaging data for moderators was done in a full intent-to-treat framework, using rigorous voxel-wise control for multiple comparisons across the whole brain. Individual-level prediction of treatment outcome was furthermore assessed using a cross-validated multivariate regression analysis.

Methods

Participants: Depressed outpatients, 18-65 years old, were recruited and assessed at four clinical sites (University of Texas Southwestern Medical Center, Massachusetts General Hospital, Columbia University, and University of Michigan; Table 1). Data reported here are based on EMBARC participants who were randomly assigned to sertraline or placebo during stage 1 of the trial (N=309). We also include data on 40 healthy individuals across the four sites to contextualize treatment-predictive brain signals relative to normative responses.

Assessments and treatment protocol: The primary clinical outcome was total scores on the Hamilton Rating Scale for Depression 17-item ($HAMD_{17}$)[24,25], administered at each study visit (baseline, week 1, week 2, week 3, week 4, week 6, and week 8).

fMRI task and acquisition parameters: The emotional conflict task is a well-characterized paradigm[17,18], that induces emotional conflict through pairing fearful and happy faces with overlaid congruent or incongruent emotion words (participants identify facial expression using a keypad). Regulation occurs via an implicit process when conflict trials are preceded by other conflict trials[11,13,17,18]. Neuroimaging acquisition parameters are shown in Table 2.

fMRI preprocessing and first-level modeling: For the emotional conflict task, the contrasts of interest were incongruent versus congruent trials (conflict) and post-incongruent incongruent trials versus post-congruent incongruent trials (an established measure of conflict regulation)[11,13,17,18].

Statistical analyses: All moderation analyses were conducted under an intention-to-treat framework, incorporating all randomized patients after removing those with excessive head motion or low task accuracy. As such, we employed linear mixed models both for the voxelwise neuroimaging data, as well as follow-up analyses on extracted brain signals, while fully controlling for any potential differences due to site of acquisition. Whole-brain voxelwise correction for multiple comparisons was performed at p<0.05 based on the false discovery rate.

Cross-validated multivariate regression analysis: To identify individual-level brain activation predictors of treatment-related change, we used a machine learning technique, i.e., Sparse Bayesian Learning (SBL), to develop a regression model, with performance evaluation by 10×10-fold cross-validation, separately for the sertraline and placebo arms (see methods). The target of the regression model was pre-minus-post $HAMD_{17}$ scores after multiple imputation, in order to maintain an intent-to-treat framework. To test the specificity of the regression model, we then applied the predictive pattern from one arm to the other arm.

Figure 2A:
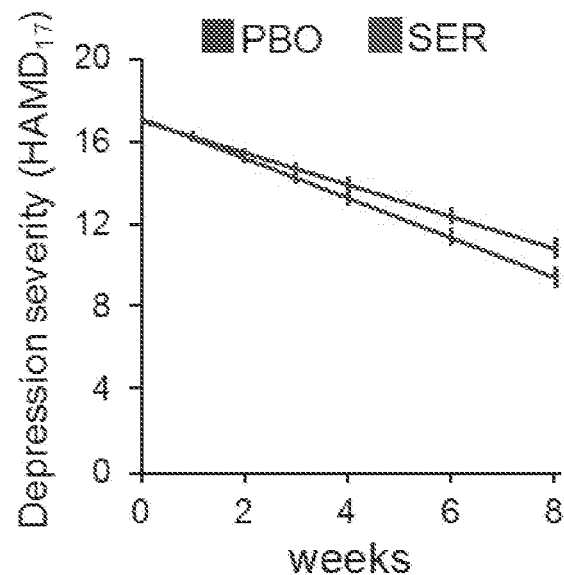
FIGS. 2A-2B. Average response across all patients to sertraline (SER) versus placebo (PBO). Shown are predicted $HAMD_{17}$ scores from the linear mixed model (FIG. 2A), and remission rates (FIG. 2B).
Figure 2B:
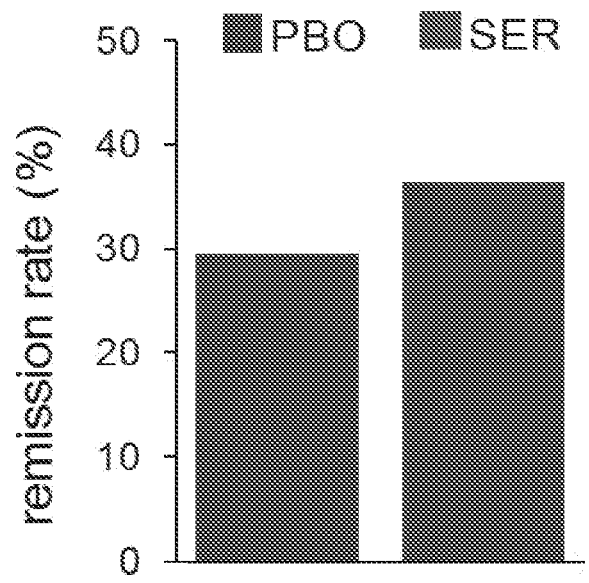

Overall effect of sertraline versus placebo: As expected from prior work[6,7], a linear mixed model on our primary $HAMD_{17}$ clinical outcome revealed a small overall numerical advantage of sertraline over placebo (endpoint symptom reduction with sertraline versus placebo: Cohen's d=0.24; remission number needed to treat (NNT)=20.1). This difference failed to meet statistical significance in the imaging sample studied here (treatment arm by time interaction F(1,222)=2.5, p=0.113; FIGS. 2A-2B).

Figure 3A:
FIGS. 3A-3E. Moderation by emotional conflict regulation-related brain activity between sertraline versus placebo.
Figure 3A:
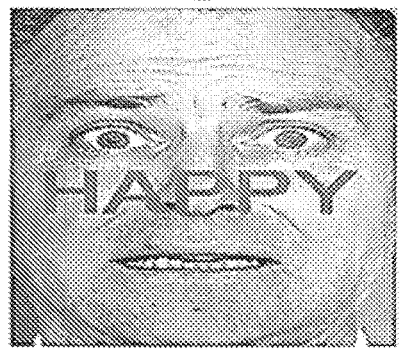

Emotional conflict moderators of treatment outcome: The emotional conflict task used here involves presentation of fearful or happy expression faces with an overlaid "FEAR" or "HAPPY" word[17,18] (FIG. 3A). The response to emotional conflict is assessed by contrasting incongruent trials (e.g. fearful face with "HAPPY" overlaid) to congruent trials (e.g. fearful face with "FEAR" overlaid)[17,18]. While emotional conflict results in slowing of reaction times, this effect can be mitigated in incongruent trials that follow incongruent trials, compared to incongruent trials that follow congruent trials[17,18]. This trial-to-trial adaptive regulation of emotional conflict reflects an active process by which the brain increases emotional control in response to prior trial conflict, which then benefits regulation of emotional conflict on the subsequent trial. Critically, this contrast between post-incongruent incongruent and post-congruent incongruent trial compares brain responses to physically identical stimuli (i.e. incongruent trials) that differ only on the relative emotional conflict regulatory context in which they come, and is furthermore independent of the incongruent versus congruent trial conflict response contrast.

Figure 3B:
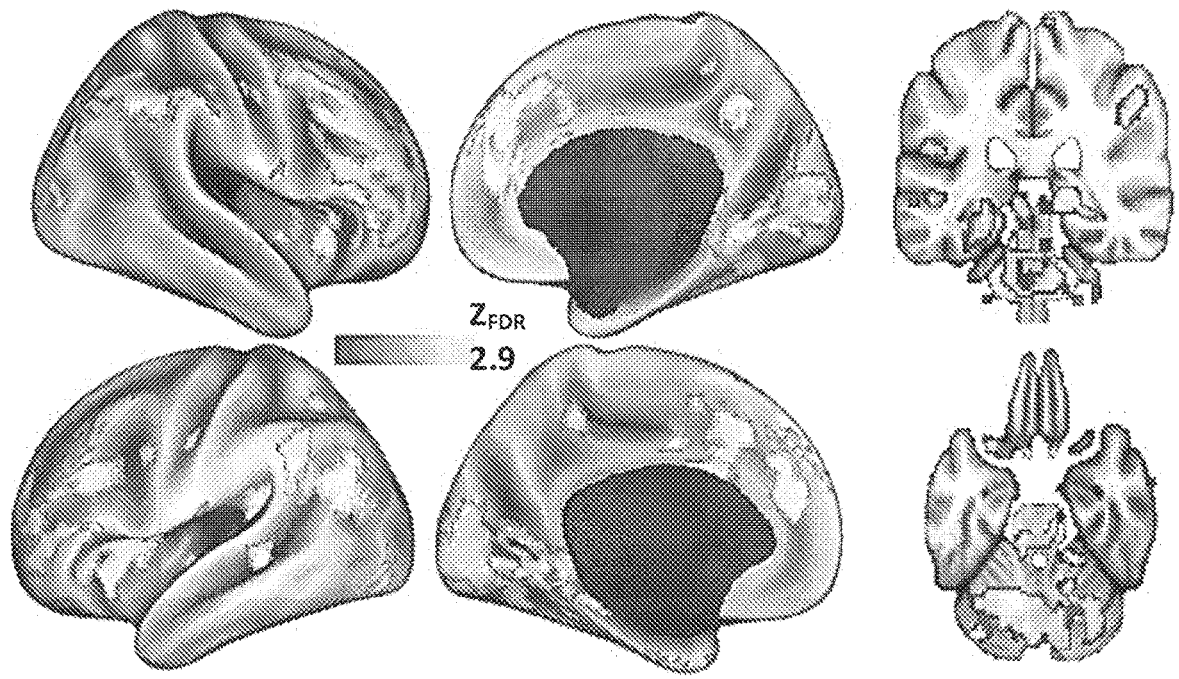
Figure 3C:
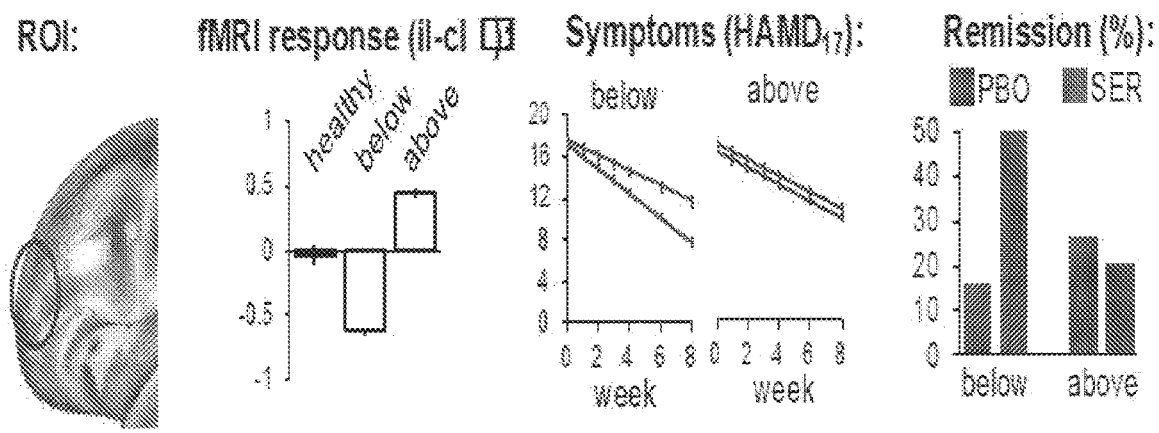
Figure 3D:
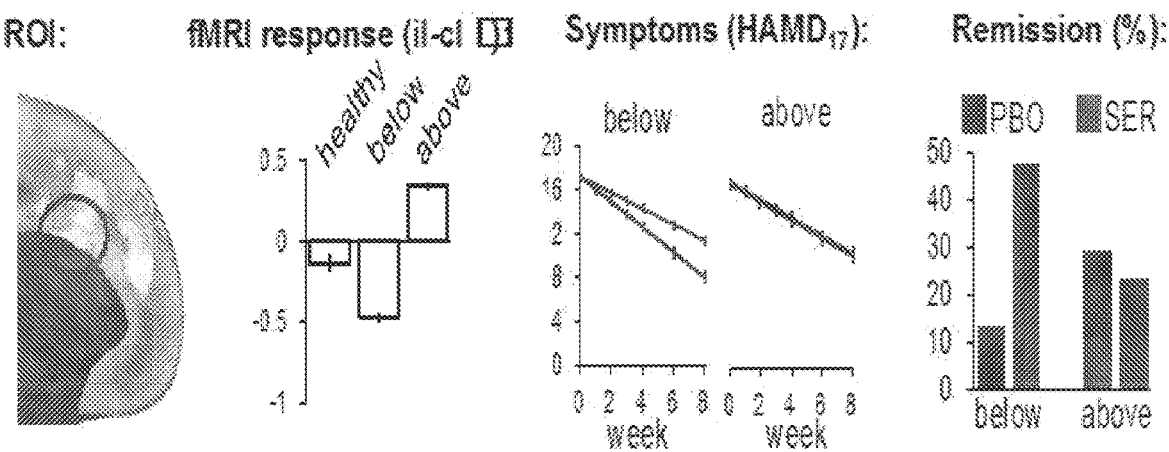
Figure 3E:
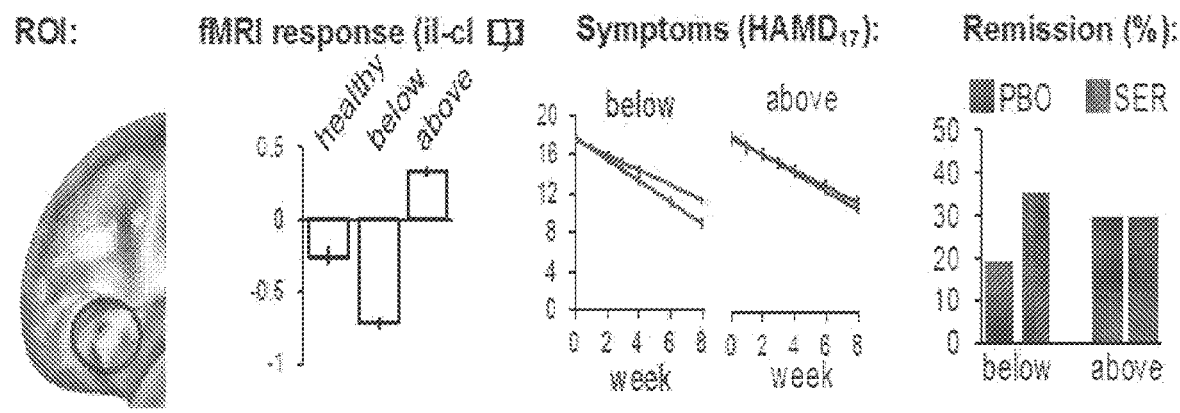

The most striking results came when examining emotional conflict regulation (post-incongruent incongruent minus post-congruent incongruent trials; iI-cI contrast). Whole-brain significant treatment moderation effects were observed in regions including the bilateral dorsolateral prefrontal and frontopolar cortices, dorsal anterior cingulate and insula, as well as the hippocampus, visual cortex and cerebellum (FIG. 3B; Tables 3-5). To better visualize these effects, we divided the depressed sample using a median split based on iI-cI activation levels, and then quantified remission rates with sertraline versus placebo for each split. Doing so revealed that individuals who best dampen activation in regions such as the frontopolar cortex (below median group remission NNT=2.9, endpoint symptom difference Cohen's d=0.85; FIG. 3C), dorsal anterior cingulate (NNT=3, d=0.79; FIG. 3D) and anterior insula (NNT=6.3, d=0.53; FIG. 3E) during emotional conflict regulation displayed superiority of sertraline over placebo. The direction of the fMRI response was consistent with, and for some patients of a greater magnitude, as that seen in healthy individuals (FIGS. 3C-3E). Unlike brain activation the iI-cI reaction time difference did not moderate treatment outcome (F=0.48, p=0.49).

Figure 4A:
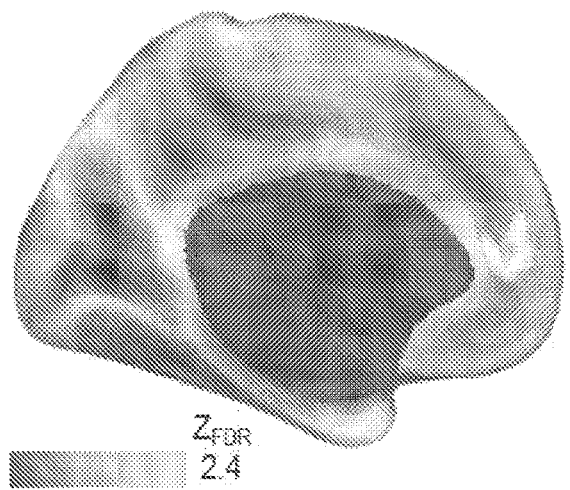
FIGS. 4A-4B. Treatment-nonspecific prediction of outcome by activation during conflict regulation.
Figure 4B:
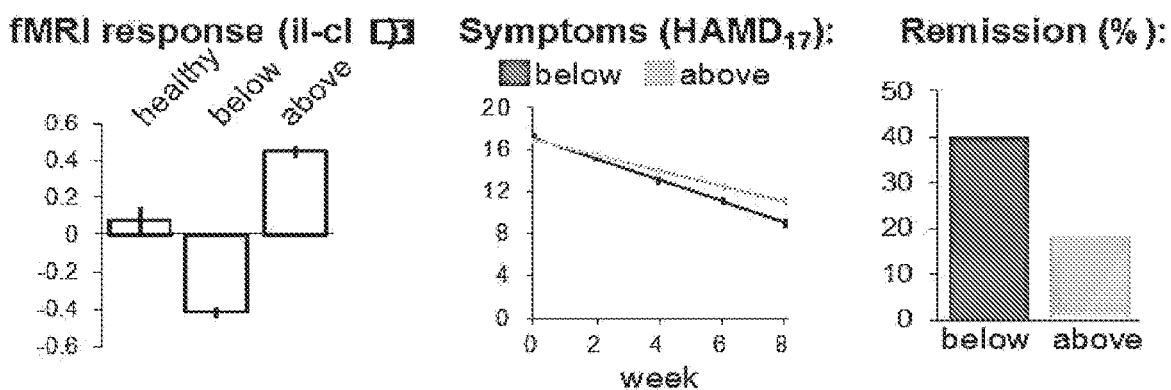
Figure 6:
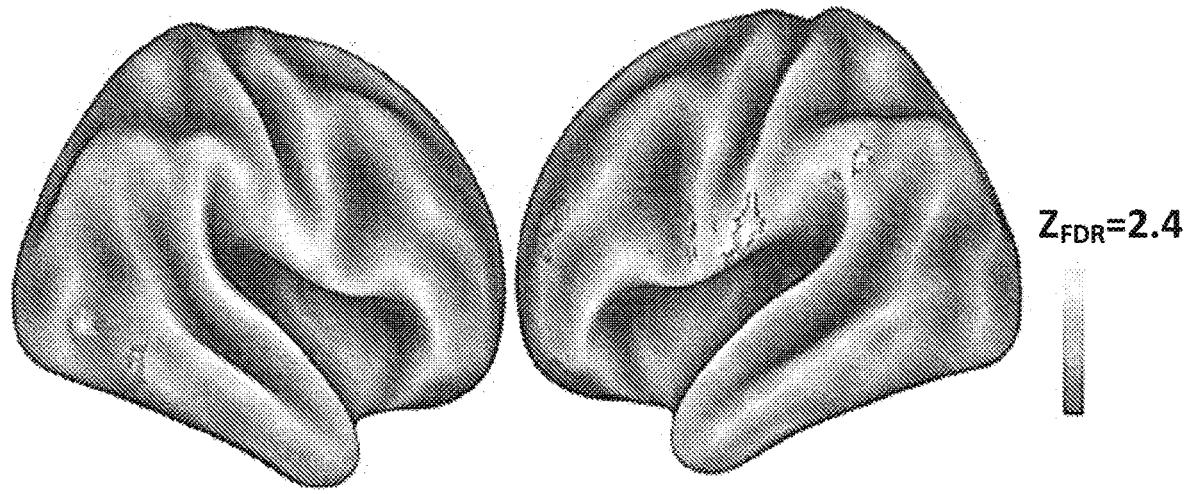
FIG. 6. Moderation of treatment outcome by activation in response to emotional conflict (I-C contrast, where I is incongruent trial and C is congruent trial).

In addition to treatment-moderation by emotional conflict regulation signals, we found that iI-cI activation in the rostral anterior cingulate predicted outcome similarly across both arms (i.e. a brain activation by time interaction; Table 6). In this case, the lower its regulation-related activation, the better were patients' outcomes across both arms (below versus above median groups remission difference NNT=4.7, endpoint symptom difference Cohen's d=0.43; FIGS. 4A-4B). This cluster furthermore overlapped with a rostral anterior cingulate cluster whose resting electroencephalography theta-frequency current source density non-specifically predicted outcome across both arms in EMBARC (data not shown)'. The brain's response to emotional conflict (incongruent minus congruent trials; I-C) also yielded whole-brain significant moderation effects, albeit in vastly fewer regions than the iI-cI contrast (FIG. 6 and Table 7).

Relationship between clinical severity measures and emotional conflict task activation: We correlated conflict regulation-related brain activity in the iI-cI contrast with several measures of baseline clinical severity, including our HAMD$_{17}$ primary measure, the Quick Inventory of Depressive Symptoms (QIDS)[27], as well as the anxious arousal, anhedonic depression and general distress subscales of the Mood and Anxiety Symptom Questionnaire (MASQ)[28]. However, no significant relationships survived FDR correction separately for each scale, suggesting that our treatment-moderating brain activation findings are not simply a marker of clinical severity.

Figure 5A:
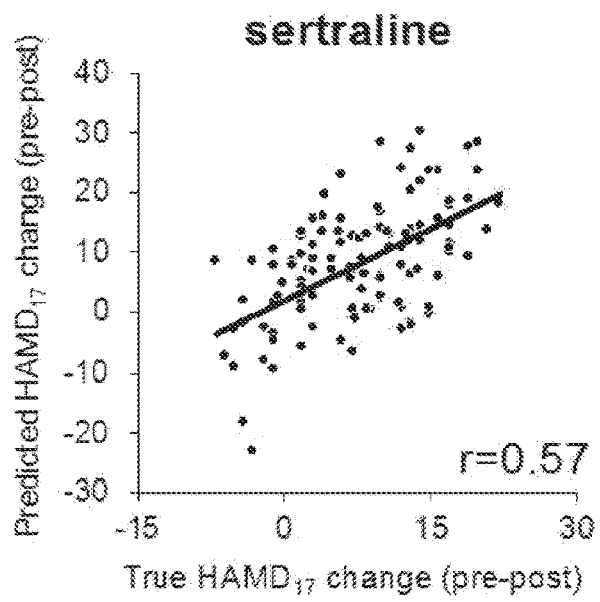
FIG. 5A-5C. Multivariate pattern regression selectively predicts response to sertraline using conflict regulation-related fMRI activity.
Figure 5B:
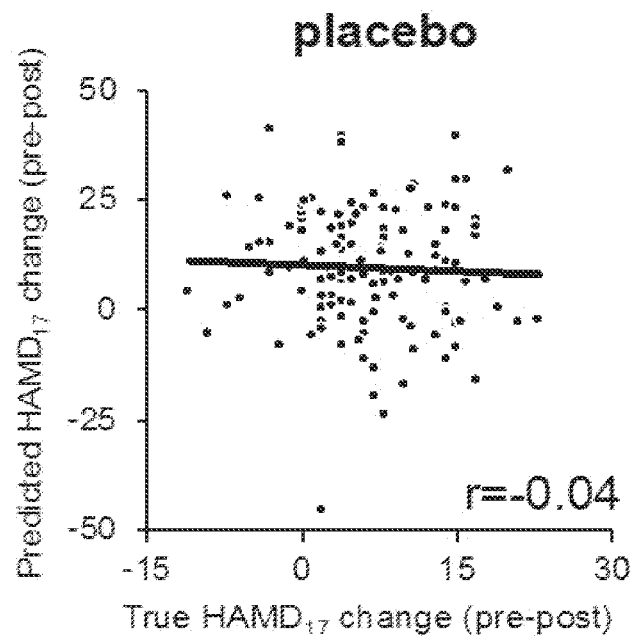
Figure 5C:
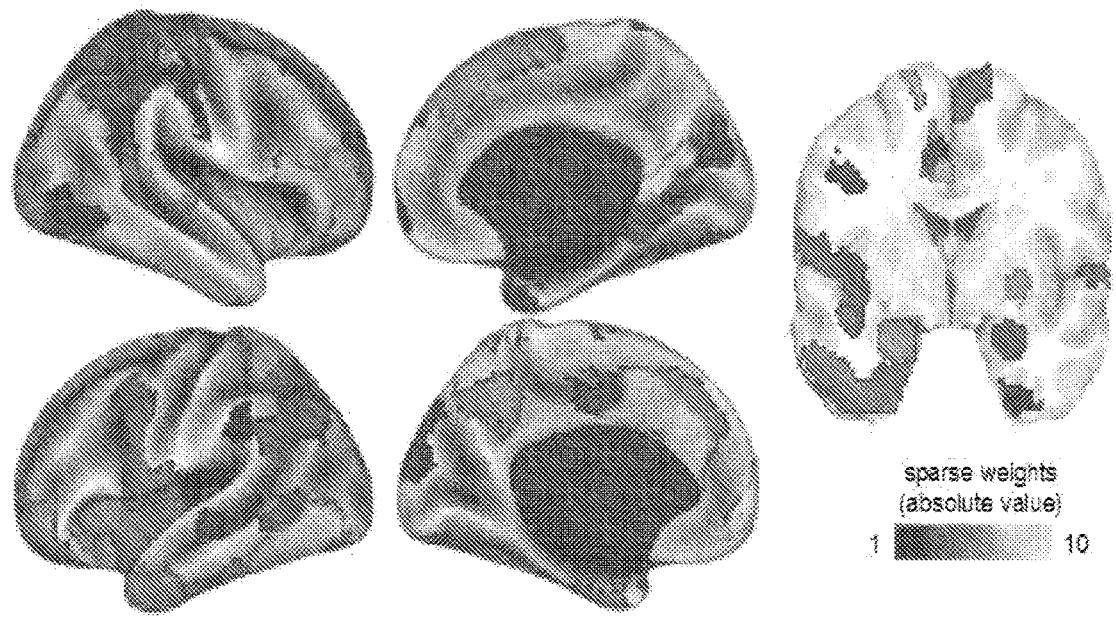
Figure 7A:
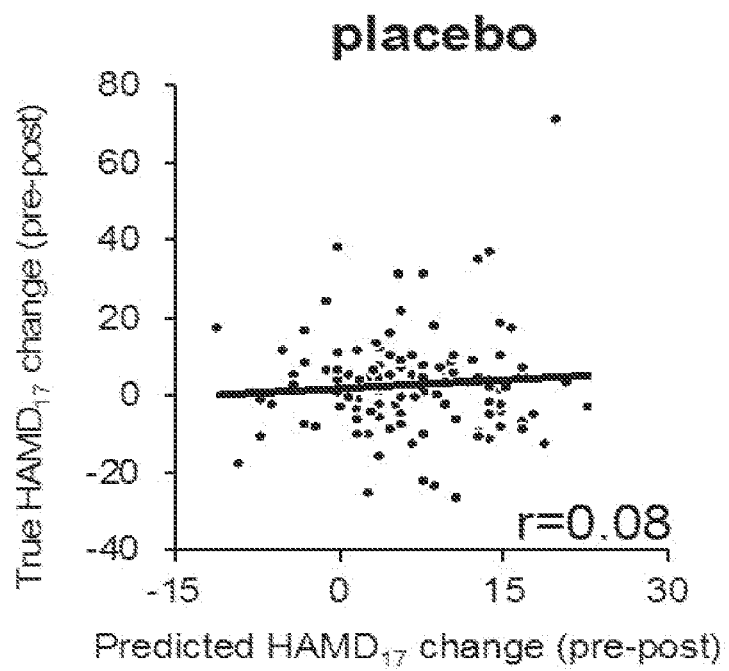
FIGS. 7A-7B. A classifier trained on pre-post symptom change in the placebo arm fail to predict outcome for placebo (FIG. 7A; =0.37) or when the placebo classifier was applied to the sertraline arm (FIG. 7B; p=0.09).
Figure 7B:
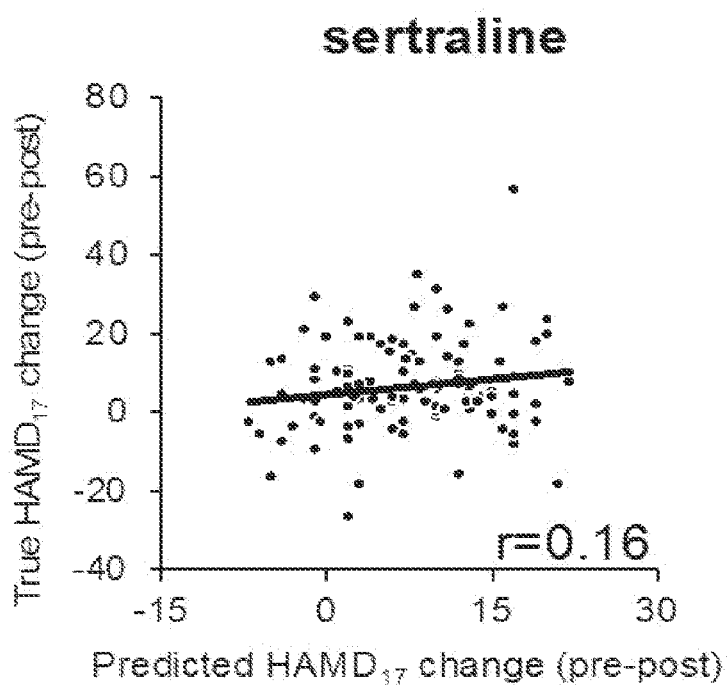

Individual level prediction through multivariate regression analysis: To assess the ability of emotional conflict regulation-related activation to predict treatment outcome at the level of individual patients, we used SBL to build a regression model for the prediction of pre-minus post-treatment change in HAMD$_{17}$. This was done in a data-driven manner by using a parcellation of the cortex and subcortex, and 10×10-fold cross-validation for prediction performance evaluation, separately for each treatment arm. A regression model trained on sertraline outcome yielded significant cross-validated prediction of observed treatment change scores (r=0.57, p<2×10$^{-11}$, permutation testing-verified p<0.0002; FIG. 5A), thus explaining 33% of variance in the effects of sertraline treatment. When applied to the placebo arm, however, this regression model failed to predict outcome (r=−0.04, p=0.66; FIG. 5B). Moreover, prediction of sertraline outcome was significantly greater than prediction of placebo outcome (Fisher's z test; z=5.28, p=6×10$^{-8}$). Interestingly, a regression model trained on placebo outcome failed to predict symptom change in either the placebo or sertraline arms (FIGS. 7A-7B). Thus, the regression model developed on sertraline outcome reflects a sertraline-specific signal that explains a substantial percentage of variance in treatment effects, separate of treatment effects including placebo responses which are inherent to both treatment arms[26]. The sertraline regression model was furthermore unrelated to clinical severity, as it failed to predict baseline HAMD$_{17}$, QIDS or MASQ scores (r's<0.07, p's>0.25). Training a regression model on baseline HAMD$_{17}$ scores likewise did not provide significant prediction result (r=−0.03, p=0.72). Regional weights driving the sertraline-predicting regression model are shown in FIG. 5C, and demonstrate a similar spatial pattern as the whole-brain voxelwise moderation analysis did in FIG. 2B.

This study tested whether the neural processes involved in emotional conflict and its regulation, a process of broad relevance for both healthy functioning and which is perturbed in major depression[14,15], can serve as a treatment outcome moderator between treatment with the SSRI sertraline and placebo. We found robust evidence for moderation primarily in the brain's trial-to-trial regulation of emotional conflict (iI-cI contrast). Most strikingly, the greater the individual's ability to dampen activation in conflict responsive regions such as the lateral prefrontal cortex, dorsal anterior cingulate, and insula during emotional conflict regulation, the greater their response to sertraline compared to placebo. By contrast, regulation-related activation in the rostral anterior cingulate predicted outcome across both treatments, essentially reflecting their shared placebo-related component. The moderation analyses were furthermore complemented by a multivariate regression analysis, which revealed a regression model that predicts sertraline-specific outcome at the individual patient level. The regression model explained 33% of the variance in sertraline-specific treatment outcome, with no confounding by placebo-related signals. Our findings thus provide strong evidence that a clinically and mechanistically meaningful stratification is possible in depression by relating biological characteristics to placebo-controlled treatment outcome. The impact of this conclusion is further reinforced by the size and methodological rigor of EMBARC as a neuroimaging-coupled placebo-controlled antidepressant RCT designed for identification of moderators, as well as the data-driven framework for all of our analyses with strict false positive control.

As such, our results provide several critical insights about depression and antidepressant treatment. First, they demonstrate that the small average clinical benefit of SSRIs over placebo in depression (here d=0.23, NNT=20.1) is in fact due to large differences in treatment outcome for some patients (i.e. ~50% remission rate with a NNT<5) but not others (i.e. ~25% remission rate and no differentiation from placebo). Moreover, this difference between patients can be identified in a predictable way based on individual differences in the brain's emotional conflict regulatory capacity. Though interventions in psychiatry have operationally treated all patients with a particular diagnosis in a similar manner, the field has long appreciated that diagnoses such as depression are composed of critical biological heterogeneity[9,29]. Thus, our findings argue that the controversy around whether SSRIs are effective relative to placebo[5-8] is better reframed as a question of what neural phenotype(s) best characterize the SSRI-responsive portion of the population of depressed patients. In other words, our moderator findings now establish a basis for personalized medicine approaches in depression.

Clinically, while a brain-based predictive test (e.g. using electroencephalography (EEG) instead of fMRI[30-33]) may prove challenging to integrate into care prior to the first antidepressant prescription, given the ease and low cost of many antidepressant medications, it may have critical utility after failure of the first agent. For example, if a patient with the non-responsive brain phenotype fails to remit with their first medication—presumably not having benefitted from a placebo response—their treatment may be best advanced by treatments with putatively distinct mechanisms of action (e.g. repetitive transcranial magnetic stimulation (rTMS), electroconvulsive therapy (ECT), or psychotherapy). Typically, patients undergo iterative rounds of pharmacological treatment for months or years prior to advancing to a treatment modality such as rTMS[34,35], leading to substantial morbidity and economic cost. More rapidly advancing patients with the SSRI non-responsive phenotype even to costly interventions such as rTMS may thus make clinical and financial sense[34,35]. It is therefore noteworthy that the large-scale studies of rTMS treatment for depression have specifically enrolled medication-resistant patients, and showed benefit of real over sham rTMS[36,37]. By contrast, individuals with an as yet undetermined level of expression of this putative SSRI-responsive brain phenotype may be best served by trying additional pharmacological interventions after an initial failure. It will therefore be important to determine whether our findings generalize to other antidepressants. It is also important to consider that pre-treatment neuroimaging in EMBARC was conducted in a medication-free state. More broadly, however, it may also be that a brain-based test that identifies an individual as having an SSRI-responsive phenotype may serve to encourage patients to seek medication treatment in the first place, and decrease the stigma associated with mental illness[38].

The treatment-moderating influence of emotional conflict regulation may furthermore hold across traditionally-defined psychiatric disorders. For example, we have recently found that greater subgenual cingulate activation during emotional conflict regulation predicted better response to psychotherapy versus wait-list in patients with post-traumatic stress disorder[39]. The ability to drive effective and targeted therapeutics based on biological stratification, including transdiagnostically, is furthermore analogous to advances in oncology. For example, mutations in the epidermal growth factor receptor endow robust responsiveness to gefitinib, which otherwise has a modest average effect size when given to unselected patients[40-42].

Importantly, we found that our emotional conflict regulation moderators were independent of baseline depression severity (assessed with various scales), and thus identify patients who are preferentially-responsive to sertraline in a manner distinct from prior suggestions that only the most clinically-severe patients benefit from antidepressants[6,7]. This furthermore builds on our prior work finding impairments in emotional conflict regulation in depression and anxiety[14,43]. Nonetheless, not all aspects of emotional conflict regulation-related activation moderated between sertraline and placebo. Activation in the rostral anterior cingulate predicted outcome independently of treatment, suggesting that it predicted the effect of the common placebo component of both interventions. This is consistent with resting electroencephalography studies, including using EMBARC data, which implicate this region in prediction of outcome with both medication and placebo[26,44]. In fact, our cluster partially overlapped with the cluster used for non-specific prediction in the electroencephalography analyses[26]. To our surprise, less regulation-related activation in this region was associated with better non-specific treatment change.

Finally, our findings provide mechanistic insights into a sertraline-responsive depression phenotype by virtue of their tie to a specific aspect of self-regulatory capacities. We, and others, have found that regions such as the dorsolateral prefrontal cortex and dorsal anterior cingulate are responsive to both emotional and non-emotional conflict[16,17]. Similar trial-to-trial regulation of emotional and non-emotional conflict occurs, and in both cases, results in reduction of activation in dorsal anterior cingulate conflict signals[45]. Hence, it may be that greater trial-to-trial regulation of any type of conflict underpins the sertraline-responsive phenotype. Identification of the importance of emotional conflict regulation also delineates a particular mental capacity, and associated brain structures, as targets for development of novel treatments. Improving emotional conflict regulation-related prefrontal dampening, assessable objectively even before symptom change is seen, through new medications, targeted stimulation, behavioral training or psychotherapy, may convert a sertraline-nonresponsive patient into a sertraline-responsive one.

In sum, these findings advance a mechanistic understanding of depression that augurs well for an effective stratification of an otherwise-heterogeneous and solely clinically-defined population based on the a priori likelihood of an individual's response to sertraline relative to placebo. We anticipate that ultimate clinical implementation (and validation) of our findings will involve transitioning from fMRI- to EEG-based brain activity measurement using the emotional conflict task[30-33]. However, the fact that a data-driven regression model can already predict 33% of the variance in sertraline-specific treatment outcome is highly encouraging (and it is unknown what the maximum proportion of medication-specific variance is even explainable). This specific predictive signal could therefore be combined with non-specific predictive signals for both medication and placebo outcome[26], explaining even more of the total variance. While other measures will no doubt further improve this stratification and aid in its broader clinical application, our work argues for a transition from questioning whether antidepressants are effective, to a focus on finding the most robust combination of moderators in order to transform research and clinical care in psychiatry. Our findings therefore provide a mechanism-driven avenue out of the general disillusionment in psychiatry with poor outcomes based on the one-size-fits-all approach that is presently the mainstay of psychiatric treatment[46].

Additional Methods

Participants and treatment: Written informed consent was obtained from each participant under institutional review board-approved protocols at each of the four clinical sites (University of Texas Southwestern Medical Center, Massachusetts General Hospital, Columbia University, and University of Michigan). Data reported here are based on EMBARC participants who were randomly assigned to sertraline or placebo during stage 1 of the trial (N=309). Key eligibility for the study included being 18-65 years old, having major depression as a primary diagnosis by the Structured Clinical Interview for DSM-IV Axis I Disorders[1], at least moderate depression severity with a score≥14 on the Quick Inventory of Depressive Symptomatology-Self Report (QIDS-SR) at screening and randomization, a major depressive episode beginning before age 30, either a chronic recurrent episode (duration≥2 years) or recurrent MDD (at least 2 lifetime episodes), and no antidepressant failure during the current episode. Exclusion criteria included: current pregnancy, breastfeeding, no use of contraception; lifetime history of psychosis or bipolar disorder; substance dependence in the past six months or substance abuse in the past two months; unstable psychiatric or general medical conditions requiring hospitalization; study medication contraindication; clinically significant laboratory abnormalities; history of epilepsy or condition requiring an anticonvulsant; electroconvulsive therapy (ECT), vagal nerve stimulation (VNS), transcranial magnetic stimulation (TMS) or other somatic treatments in the current episode; medications (including but not limited to antipsychotics and mood stabilizers); current psychotherapy; significant suicide risk; or failure to respond to any antidepressant at adequate dose and duration in the current episode. In addition, 40 healthy individuals who were medically and psychiatrically healthy, were recruited across the four sites, and assessed in a similar manner as the patients.

Clinical trial: EMBARC used a double-blind design, wherein participants were randomized to an 8-week course of sertraline or placebo. Randomization was stratified by site, depression symptoms severity, and chronicity using a block randomization procedure. Sertraline dosing began at 50 mg using 50 mg capsules and was increased as tolerated if the patient did not respond until a maximum of 200 mg[2]. A similar dosing approach was used for placebo capsules.

Emotional conflict task: This well-characterized paradigm assesses both emotional conflict and emotional conflict regulation[3,4]. Each trial involved presentation of an emotional face with either a fearful or happy expression, drawn from the set of Ekman & Friesen[5], with an overlaid emotion word ("FEAR" or "HAPPY"). Participants were instructed to identify the facial emotion with a key press, while trying to ignore the emotion word. The task consisted of 148 trials, with stimuli presented for 1000 milliseconds (ms) in a fast event-related design. Interstimulus intervals were 3000-5000 ms in a pseudo-randomized order counterbalanced for facial expression, gender, word, and response button.

Stimuli were either congruent (e.g. fearful face with "FEAR") or incongruent (e.g. fearful face with "HAPPY"), and stimuli were furthermore balanced to achieve an equal fraction of current and prior trial congruency, while ensuring no direct stimulus repetitions. Prior to performance of the task during neuroimaging, all participants underwent a practice version to ensure task proficiency was reached (minimum 80% accuracy) and the task instructions were understood. The neuroimaging task lasted 13 minutes and 14 seconds.

fMRI preprocessing and first-level modeling: FSL tools were used to preprocess imaging data[6,7]. Functional images were first realigned to structural images using an affine registration matrix and boundary-based registration based upon tissue segmentation as implemented in FSL's FLIRT, which was concatenated with a non-linear normalization of each participant's T1 image to the Montreal Neurological Institute (MNI) 152-person 1 mm3 T1 template using FNIRT from FSL 5.0 to result in a single transformation step from individual native functional space to structurally-aligned and spatially-normalized template space. Functional images were realigned to the middle volume of the run. Nuisance signals corresponding to segmented white matter and CSF were regressed out of motion-corrected functional images. A 6 mm full-width half max (FWHM) isotropic smoothing kernel was then applied to preprocessed time series images to account for individual anatomical variability.

For individual-level analyses for each participant and timepoint, regressors modeling trials of interest were convolved with the hemodynamic response function. First-level general linear models were estimated in SPM 8[8]. Regressors corresponded to zero-duration markers set at the onset of stimuli, which were explicitly categorized by congruency (Incongruent or Congruent) and prior trial type (Post-incongruent or Post-congruent) in order to model conflict response and regulation effects. This resulted in 4 different trial types in total, in addition to nuisance regressors for error trials and post-error trials (when applicable) and six motion parameters.

Participant selection and quality control procedures: In order to assure the quality of imaging measures in testing moderation and prediction effects, consistent with our prior work in imaging treatment effects[9,10], we instituted cutoffs for absolute level of motion (root mean square of the absolute level of movement<4 mm across the mean of the squared maximum displacements in each of the 6 translational and rotational parameters estimated during realignment) during the baseline and week 1 scans. In addition, in order to ensure brain activation measures reflect task-relevant metrics, we also instituted a minimum level of behavioral accuracy during completion of the emotional conflict task as an additional quality control metric (total accuracy≥80% of trials correct). Functional runs at baseline displaying motion higher than our cutoff OR accuracy below the minimum cutoff were excluded from group-level analyses.

Statistical analyses: Assessing the effect of sertraline on depressive symptoms: Using the total sample after quality control procedures for poor quality imaging data, repeated measures of $HAMD_{17}$ total score at baseline, week 1, week 2, week 3, week 4, week 6, and week 8 (endpoint) were entered into a longitudinal linear mixed model in IBM SPSS version 21.0[11] along with variables coding for participant, treatment arm, site (three centered dummy coded variables, each specifying one of the non-UT Southwestern study sites vs. UT Southwestern) and time (scaled from 0 to 1) to assess the effect of sertraline vs. placebo on depression symptoms in an intent-to-treat framework. Treatment arm was effects coded as −0.5 for placebo and 0.5 for sertraline. Random effects were specified for the model intercept and the effect of time on symptoms to account for within-participant variation in baseline depressive symptom severity as well as unobservable contributors to differential symptom change over time that could not be directly attributed to the intervention (sertraline or placebo). A fixed intercept as well as a fixed effect of time, effect of Columbia vs. UT Southwestern site, effect of Massachusetts General Hospital vs. UT Southwestern site, effect of University of Michigan vs. UT Southwestern site, and treatment arm×time were modeled, with the latter interaction effect of interest specifying differential trajectories in symptom change over time for sertraline vs. placebo while controlling for baseline severity (random intercept), non treatment-specific symptom changes (time), and potential differences in site cohorts.

Assessing baseline brain activation moderation of the sertraline vs. placebo effect: For each contrast of interest (iI-cI and inc-con), first-level, spatially-normalized activation contrast maps from each individual were loaded into $R^{12}$ using the fmri package[13]. We constrained analyses to a search space defined by a whole-brain mask constructed from: a) a 30% probabilistic voxelwise threshold derived from spatially normalized, segmented binary gray matter images from an independent sample of healthy comparison participants[9,10]; and b) a conjunction map of adequate signal coverage across study scanners constructed by concatenating the binarized individual-level average map of all task experimental conditions within participants acquired at each scanner, thresholding at a minimum of 50% coverage within each scanner sample, and then conjoining these maps across all scanners. Thus, the final search space was a function of both adequate signal coverage across all study scanners as well as a probabilistic assignment to the brain's gray matter. At each voxel within this search space, the moderating effect of baseline brain activation (mean-centered) was examined using a longitudinal linear mixed model implemented in the nlme R package.[14] Modeled effects included a random and fixed intercept, fixed effects of time, time×treatment arm, 4 mean-centered, dummy-coded scanner variables corresponding to: a) Columbia University scanner 1 vs. UT Southwestern scanner; b) Columbia University scanner 2 vs. UT Southwestern scanner; c) Massachusetts General Hospital scanner vs. UT Southwestern scanner; and d) University of Michigan scanner vs. UT Southwestern scanner, treatment arm×time×brain activation, and all model variables in interaction with each of the 4 site variables. The effect of interest was the treatment arm×time×brain activation moderation effect from this model, which included all lower-order and higher-order interaction terms with each of the scanner variables to fully control for potential effects due to this source of heterogeneity. At each voxel, the number of degrees of freedom was individually-defined based upon the number of individuals displaying adequate signal coverage at that voxel (which tended to be less in areas prone to EPI BOLD signal dropout, particularly for certain scanners), with individuals displaying "0" values for activation being removed from the analysis. At each voxel, the relevant F tests corresponding to effects of interest were transformed to p-values and then z-values to nullify potential statistical variation across voxels secondary to varying degrees of freedom and signal coverage. These Z value maps for effects of interest were then written out to NIFTI files using the fmri package, and voxel-level FDR-correction within the whole-brain specified search space (see above) was conducted using AFNI's program 3 dFDR. Voxels displaying FDR-corrected Z-values<1.96 (q<0.05) were then thresholded and clustered for subsequent individual-level extraction and visualization of effects in IBM SPSS version 21.0[11].

Multivariate Regression Analysis: Sparse Bayesian learning (SBL) was used to build a regression model for the prediction of pre-minus post-treatment change in $HAMD_{17}$. By exploiting an automatic relevance determination prior to penalizing unnecessary complexity in the model, SBL is able to automatically determine the feature sparsity under a Bayesian evidence framework[17]. The effectiveness of the popular L1-regularization based sparse learning algorithms[15] depends on the selection of regularization hyperparameter to a large extent. Cross-validation on training set has been usually used to determine the most appropriate hyperparameter. However, additional validation data from the training set are required by cross-validation for hyperparameter selection, which is prone to overfitting since fewer training samples can be used for model calibration[16]. Different from the L1-regularization approaches, all model parameters in SBL can be efficiently estimated based on all available training data without the need of cross-validation. SBL therefore provides a more accurate estimation of the sparse solution compared with other L1-regularization based sparse learning algorithms[18], especially when a small training set is available. In the past decades, SBL has demonstrated its strength in various fields including EEG classification for brain-computer interface[19] and bioinformatics analysis of gene expression data[20,21].

SBL was conducted on data from patients who had baseline $HAMD_{17}$, passed the image and task accuracy quality control criteria for the baseline scan, and had imaging data at baseline (sertraline N=115, placebo N=122). For participants lacking an endpoint $HAMD_{17}$, multiple imputation by chained equations was conducted in $R^{12}$ using the package mice[22]. The following observed variables were utilized in order to impute endpoint $HAMD_{17}$ values for missing data via Bayesian regression: baseline $HAMD_{17}$, week 1 $HAMD_{17}$, week 2 $HAMD_{17}$, week 3 $HAMD_{17}$, week 4 $HAMD_{17}$, week 6 $HAMD_{17}$, baseline Quick Inventory of Depressive Symptoms (QIDS) total score, baseline Mood and Symptom Questionnaire subscale scores for Anxious Arousal, Anhedonic Depression, and General Distress, Snaith-Hamilton Pleasure Scale (SHAPS) total score, age, years of education, gender, and Wechsler Abbreviated Scale of Intelligence (WASI) t-scores for Vocabulary and Matrix Reasoning. Extractions were conducted on 200 cortical regions of interest (ROIs), defined based on a recently-published cortical parcellation derived from applying a combination of local gradient analysis and global signal similarity on an independent resting-state fMRI cohort[23]. ROIs were mapped to seven previously identified functional networks based on the spatial overlap between each ROI and each network[23]. In addition to these cortical ROIs, subcortical ROIs included striatal[24] and cerebellar[25] parcellations based on the same seven functional networks, amygdala ROIs[26], anterior and posterior hippocampal ROIs[27] and the thalamus[28]. We then regressed imaging site out of these data using multiple linear regression, and the residualized brain signals were then used for SBL-based prediction.

A regression model was then built based on SBL to predict each individual's pre-minus-post change in $HAMD_{17}$ scores, wherein the most important ROI features were determined under a probabilistic framework by exploiting a separate Gaussian prior with a Gaussian likelihood function. All model parameters for controlling the sparsity of regression weights were automatically estimated through Bayesian machine learning based on each training set. The prediction performance was evaluated by 10×10 cross-validation. Specifically, for 10 repetitions, all participants were randomly divided into 10 folds, such that each participant was left out and used as a test set once while the remaining nine folds were used as a training set for SBL model learning. Each participant was left out exactly once after running each 10-fold cross-validation. By using the estimated regression weights of the SBL model, we computed the predicted symptom change value for each of the left-out participants by the weighted sum of the all 235 ROI features. After repeating 10-fold cross-validation 10 times, we determined each participant's predicted symptom change by taking the median of the predicted values across each of the 10 times that participant was left out. Pearson's correlation coefficient was then computed by correlating the predicted symptom changes and the actual symptom changes across all participants. The outcome of SBL was assessed by correlating model-predicted $HAMD_{17}$ change scores with observed/imputed change scores. Significant correlations were verified using 5,000 permutations of the SBL modeling conducted by randomly shuffling observed/imputed change scores across participants. Specificity of the model prediction was tested by applying, at each round of cross-validation, the regression model (with appropriate intercepts) to the data from the other treatment arm, which was summarized for each participant by taking the median of the 10 rounds of cross-validation.

TABLE 1

Baseline sociodemographic and clinical variables. Statistics reflect comparisons of the Sertraline and Placebo arms.

| | Healthy | | Sertraline | | Placebo | | | |
| --- | --- | --- | --- | --- | --- | --- | --- | --- |
| Categorical variables | n | % | n | % | n | % | $X^2$ | P value |
| Gender | | | | | | | 1.73 | 0.19 |
| Male | 15 | 37.5 | 34 | 27.90 | 47 | 36.40 | | |
| Female | 25 | 62.5 | 88 | 72.10 | 82 | 63.60 | | |
| Race | | | | | | | 1.22 | 0.54 |
| White | 26 | 65.0 | 78 | 63.90 | 90 | 69.80 | | |
| African American | 9 | 22.5 | 25 | 20.50 | 20 | 15.50 | | |
| Other | 5 | 12.5 | 19 | 15.60 | 19 | 14.70 | | |
| Employment status | | | | | | | 0.03 | 0.86 |
| Employed | 31 | 77.50 | 68 | 55.74 | 74 | 57.36 | 0.17 | 0.92 |

TABLE 1-continued

Baseline sociodemographic and clinical variables. Statistics reflect comparisons of the Sertraline and Placebo arms.

| | | | | | | | | |
|---|---|---|---|---|---|---|---|---|
| Unemployed | 7 | 17.50 | 50 | 40.98 | 50 | 38.76 | | |
| N/A or Missing | 2 | 5.00 | 4 | 3.28 | 5 | 3.88 | | |

| Continuous variables | | | Mean | SD | Mean | SD | t value | p value |
|---|---|---|---|---|---|---|---|---|
| Age | 37.63 | 14.85 | 36.79 | 13.38 | 36.36 | 12.66 | −0.26 | 0.79 |
| Age of onset | N/A | N/A | 16.04 | 6.15 | 16.23 | 5.58 | 0.26 | 0.80 |
| Years of education | 15.16 | 2.26 | 15.06 | 2.68 | 15.14 | 2.66 | 0.22 | 0.83 |
| Number of MDE | N/A | N/A | 30.86 | 115.36 | 26.50 | 111.19 | −0.31 | 0.76 |
| Duration of current episode | N/A | N/A | 42.63 | 70.40 | 49.11 | 115.56 | 0.53 | 0.60 |
| HAMD$_{17}$ | N/A | N/A | 18.66 | 4.65 | 18.79 | 4.22 | 0.24 | 0.81 |
| Medication dose | N/A | N/A | 101.93 | 34.41 | 108.96 | 29.48 | 1.61 | 0.11 |

Note.
MDE = major depression episodes;
*20 MDD participants (10 with placebo, and 11 with sertraline) with too many episodes to count; 6 MDD participants (4 placebo, and 2 with sertraline) with no employment status.

TABLE 2

Structural MRI and fMRI acquisition scanning parameters.

| | CU | MGH | TX | UM |
|---|---|---|---|---|
| Scanner | General Electric 3 T | Siemens 3 T | Phillips 3 T | Phillips 3 T |
| Structural | Series = IR FSPGR<br>TR/TE = 6.0 ms/2.4 ms<br>Flip Angle = 9°<br>Thickness = 1 mm<br>Resolutions =1 × 1 mm$^2$<br>Duration = 5 min | Series = MPRAGE<br>TR/TE = 2.3 s/2.54 ms<br>Flip Angle = 9°<br>Thickness = 1 mm<br>Resolutions = 1 × 1 mm$^2$<br>Durations = 4.30 min | Series = MPRAGE<br>TR/TE = 8 ms/3.7 ms<br>Flip Angle = 12°<br>Thickness = 1 mm<br>Resolutions = 1 × 1 mm$^2$<br>Durations = 4.24 min | Series = TFE<br>TR/TE = 8.1 ms/3.7 ms<br>Flip Angle = 12°<br>Thickness = 1 mm<br>Resolutions = 1 × 1 mm$^2$<br>Duration = 5.29 min |
| rsfMRI | TR/TE = 2000/28 msec<br>Flip Angle = 90°<br>Res. = 3.2 × 3.2 mm$^2$<br>Thickness = 3.1 mm<br>Matrix = 64 × 64 | TR/TE = 2000/28 msec<br>Flip Angle = 90°<br>Res. = 3.2 × 3.2 mm$^2$<br>Thickness = 3.1 mm<br>Matrix = 64 × 64 | TR/TE = 2000/28 msec<br>Flip Angle = 90°<br>Res. = 3.2 × 3.2 mm$^2$<br>Thickness = 3.1 mm<br>Matrix = 64 × 64 | TR/TE = 2000/28 msec<br>Flip Angle = 90°<br>Res. = 3.2 × 3.2 mm$^2$<br>Thickness = 3.1 mm<br>Matrix = 64 × .64 |

TABLE 3

Whole-Brain Treatment Outcome-Moderating Conflict Regulation (iI-cI) Activation. The large prefrontal and posterior clusters are broken down further in Tables 4 and 5, respectively.

| Hem. | MNI Atlas Region(s) | # Voxels | X | Y | Z | Voxel Stats FDR Z Mean | SD | Extractions Parameter (Sig.) Sertraline | Placebo |
|---|---|---|---|---|---|---|---|---|---|
| L/R | Middle Orbital Gyri/Inferior Frontal Gyri (Pars Orbitalis & Pars Triangularis)/Insula Lobe/Middle Frontal Gyri/Superior Frontal Gyri/Superior Medial Gyri/Anterior Cingulate Cortex/Middle Cingulate Cortex/Medial Frontal Gyri [see individual peaks within the cluster in supplemental table 4] | 10537 | −38 | 48 | 12 | 2.30 | 0.24 | 6.40 (<0.001) | −3.29 (0.016) |
| L/R | Cerebellum/Inferior Temporal Gyri/Fusiform Gyri/Lingual Gyri/Parahippocampal Gyri/Hippocampi/Inferior Occipital Gyri/Calcarine Gyri/Middle Temporal Gyri/Thalamus/Middle Occipital Gyri/Superior Occipital Gyri/Precuneus/Cuneus [see individual peaks within the cluster in supplemental table 5] | 10470 | −14 | −44 | 0 | 2.25 | 0.21 | 3.65 (0.002) | −4.30 (0.001) |
| R | Angular Gyrus/Middle Occipital Gyrus/Superior Occipital Gyrus/Supramarginal Gyrus/Inferior Parietal Lobule/Superior Parietal Lobule | 1829 | 38 | −64 | 48 | 2.29 | 0.22 | 1.72 (0.102) | −3.13 (0.003) |

TABLE 3-continued

Whole-Brain Treatment Outcome-Moderating Conflict Regulation (iI-cI) Activation. The large prefrontal and posterior clusters are broken down further in Tables 4 and 5, respectively.

| Hem. | MNI Atlas Region(s) | # Voxels | X | Y | Z | Voxel Stats FDR Z Mean | SD | Extractions Parameter (Sig.) Sertraline | Placebo |
|---|---|---|---|---|---|---|---|---|---|
| L | Middle Occipital Gyrus/Middle Temporal Gyrus/Superior Temporal Gyrus/Supramarginal Gyrus/Angular Gyrus/Inferior Parietal Lobule/ | 1262 | −48 | −50 | 34 | 2.26 | 0.22 | 4.61 (0.002) | −3.86 (0.003) |
| R | Cerebellum | 119 | 38 | −48 | −38 | 2.21 | 0.20 | 4.21 (0.003) | −3.14 (0.016) |
| R | Insula Lobe | 103 | 46 | 4 | 0 | 2.24 | 0.21 | 5.86 (<0.001) | −0.68 (0.537) |
| L | Fusiform Gyrus | 102 | −28 | −4 | −38 | 2.32 | 0.24 | 2.77 (0.051) | −2.89 (0.008) |
| R | Precuneus | 98 | 10 | −52 | 38 | 2.15 | 0.12 | 1.73 (0.089) | −1.81 (0.031) |
| L | Postcentral Gyrus | 83 | −54 | −16 | 20 | 2.23 | 0.18 | 1.73 (0.079) | −1.79 (0.048) |
| L | Medial Temporal Pole | 81 | −32 | 14 | −36 | 2.25 | 0.20 | 0.64 (0.648) | −3.63 (0.001) |
| L | Middle Cingulate Cortex | 75 | −6 | −4 | 42 | 2.09 | 0.09 | 2.94 (0.008) | −2.59 (0.039) |
| L | Postcentral Gyrus | 67 | −46 | −14 | 34 | 2.09 | 0.10 | 1.89 (0.093) | −1.94 (0.056) |
| R | Superior Temporal Gyrus | 64 | 42 | −18 | −4 | 2.16 | 0.18 | 3.63 (0.004) | −4.75 (0.029) |
| L | Middle Frontal Gyrus | 57 | −28 | 8 | 56 | 2.11 | 0.10 | 4.03 (0.002) | −2.32 (0.145) |
| R | Precentral Gyrus | 55 | 42 | −16 | 40 | 2.12 | 0.11 | 2.25 (0.05) | −2.42 (0.017) |
| L | Precuneus | 50 | −10 | −44 | 46 | 2.13 | 0.12 | 2.59 (0.023) | −2.04 (0.028) |
| R | Caudate Nucleus | 48 | 14 | 12 | 16 | 2.07 | 0.08 | 2.52 (0.172) | −2.97 (0.054) |
| L | Precentral Gyrus | 39 | −48 | 4 | 30 | 2.14 | 0.13 | 1.04 (0.248) | −2.32 (0.013) |
| L | Superior Frontal Gyrus | 39 | −14 | 20 | 68 | 2.21 | 0.15 | 1.38 (0.084) | −2.89 (0.004) |
| R | Inferior Frontal Gyrus (Pars Opercularis) | 37 | 56 | 14 | −2 | 2.14 | 0.14 | 1.19 (0.11) | −1.45 (0.035) |
| R | Middle Temporal Gyrus | 36 | 66 | −2 | −16 | 2.18 | 0.16 | −5.24 (<0.001) | 0.66 (0.543) |
| R | Cuneus | 36 | 16 | −64 | 34 | 2.12 | 0.10 | 2.29 (0.040) | −1.18 (0.204) |
| L | Cerebellum | 31 | −46 | −74 | −34 | 2.09 | 0.08 | 0.39 (0.652) | −3.17 (0.001) |
| L | Superior Temporal Gyrus | 31 | −44 | −10 | −14 | 2.22 | 0.22 | −1.97 (0.126) | 4.72 (0.001) |
| R | Paracentral Lobule | 28 | 14 | −44 | 54 | 2.05 | 0.06 | 2.07 (0.123) | −3.60 (0.003) |
| R | Paracentral Lobule | 28 | 10 | −36 | 78 | 2.23 | 0.18 | −1.56 (0.032) | 1.34 (0.111) |
| L | Superior Temporal Gyrus | 27 | −44 | −14 | −2 | 2.25 | 0.19 | 1.48 (0.09) | −2.53 (0.011) |
| R | Postcentral Gyrus | 24 | 68 | 0 | 16 | 2.11 | 0.12 | 2.77 (0.039) | −2.60 (0.010) |
| R | Superior Medial Gyrus | 22 | 2 | 32 | 62 | 2.16 | 0.15 | 1.58 (0.018) | −0.79 (0.223) |
| L | Insula Lobe | 21 | −26 | 16 | −20 | 2.17 | 0.12 | 0.04 (0.972) | 5.10 (<0.001) |

X, Y, and Z values are cluster peak coordinates in MNI stereotactic space;
Voxel stats column depicts the mean and standard deviation of the voxelwise statistics for each cluster's effect;
Extractions column reports the parameter and significance value for the activation moderator × time effect within each treatment arm using extracted individual cluster beta values for each participant;
FDR = false discovery rate;
Hem = hemisphere;
L = left;
R = right;
Sig. = significance.

TABLE 4

Prefrontal Cluster from Supplemental Table 3 Outcome-Moderating Conflict Regulation (iI-cI) Activation.

| Hem. | MNI Atlas Region(s) | X | Y | Z | Voxel Stats FDR Z Mean | SD | Extractions Parameter (Sig.) Sertraline | Placebo |
|---|---|---|---|---|---|---|---|---|
| R | Middle Frontal Gyrus | 51 | 33 | 21 | 2.67 | 0.20 | 2.05 (0.037) | −3.09 (0.002) |
| L | Middle Frontal Gyrus | −36 | 48 | 16 | 2.70 | 0.13 | 3.63 (<0.001) | −1.06 (0.211) |
| R | Superior Frontal Gyrus | 26 | 57 | 10 | 2.76 | 0.12 | 2.50 (0.006) | −2.78 (0.001) |
| L | Superior Medial Gyrus | −9 | 17 | 43 | 2.59 | 0.22 | 4.88 (<0.001) | −3.13 (0.026) |
| R | Middle Frontal Gyrus | 44 | 23 | 36 | 2.68 | 0.16 | 2.87 (0.05) | −2.19 (0.010) |
| L | Anterior Cingulate Cortex | −3 | 11 | 26 | 2.60 | 0.22 | 5.58 (<0.001) | −1.82 (0.151) |
| R | Superior Medial Gyrus | 3 | 39 | 32 | 2.62 | 0.18 | 3.81 (<0.001) | −1.05 (0.155) |
| L | Superior Medial Gyrus | −11 | 43 | 23 | 2.49 | 0.21 | 6.31 (<0.001) | −0.27 (0.802) |
| R | Middle Orbital Gyrus | 36 | 57 | −2 | 2.43 | 0.25 | 1.49 (0.044) | −2.08 (0.012) |
| L | Insula Lobe | −32 | 15 | 14 | 2.45 | 0.22 | 4.09 (0.002) | −1.48 (0.197) |
| L | Superior Frontal Gyrus | −18 | 65 | 15 | 2.56 | 0.15 | 2.82 (0.001) | −2.28 (0.004) |
| R | Middle Frontal Gyrus | 23 | 51 | 29 | 2.48 | 0.19 | 2.47 (0.014) | −3.25 (0.001) |
| L | Inferior Frontal Gyrus (Pars Triangularis) | −36 | 28 | −1 | 2.44 | 0.23 | 3.20 (0.004) | −2.79 (0.020) |
| L | Inferior Frontal Gyrus (Pars Triangularis) | −38 | 20 | 23 | 2.49 | 0.18 | 2.46 (0.012) | −2.20 (0.019) |
| L | Insula Lobe | −39 | 17 | 3 | 2.43 | 0.19 | 3.87 (<0.001) | −0.39 (0.634) |
| R | Inferior Frontal Gyrus (Pars Triangularis) | 45 | 23 | 3 | 2.40 | 0.20 | 3.23 (0.001) | −1.13 (0.159) |

TABLE 4-continued

Prefrontal Cluster from Supplemental Table 3 Outcome-Moderating Conflict Regulation (iI-cI) Activation.

| Hem. | MNI Atlas Region(s) | X | Y | Z | Voxel Stats FDR Z Mean | SD | Extractions Parameter (Sig.) Sertraline | Placebo |
|---|---|---|---|---|---|---|---|---|
| L | Middle Orbital Gyrus | −36 | 51 | −6 | 2.40 | 0.21 | 2.13 (0.041) | −2.17 (0.016) |
| R | Middle Frontal Gyrus | 37 | 13 | 44 | 2.37 | 0.17 | 4.49 (0.004) | −2.01 (0.052) |
| L | Insula Lobe | −41 | 6 | 8 | 2.35 | 0.19 | 1.90 (0.118) | −2.38 (0.035) |
| R | Right Superior Medial Gyrus | 10 | 62 | 32 | 2.43 | 0.24 | 1.47 (0.034) | −2.21 (0.001) |
| L | Inferior Frontal Gyrus (P. Triangularis) | −51 | 24 | 30 | 2.33 | 0.20 | 1.76 (0.057) | −1.83 (0.012) |

X, Y, and Z values are the peak coordinates in MNI stereotactic space from the large prefrontal cluster;

Voxel stats column depicts the mean and standard deviation of the voxelwise statistics for a 6 mm radius sphere centered around the peak;

Extractions column reports the parameter and significance value for the activation moderator × time effect within each treatment arm using extracted individual peak sphere beta values for each participant;

FDR = false discovery rate;

Hem = hemisphere;

L = left;

R = right;

Sig. = significance.

TABLE 5

Posterior Cluster from Table 3 Outcome-Moderating Conflict Regulation (iI-cI) Activation.

| Hem. | MNI Atlas Region(s) | X | Y | Z | Voxel Stats FDR Z Mean | SD | Extractions Parameter (Sig.) Sertraline | Placebo |
|---|---|---|---|---|---|---|---|---|
| R | Cerebellum | 19 | −72 | −36 | 2.41 | 0.24 | 3.05 (0.029) | −2.53 (0.031) |
| L | Lingual Gyrus | −13 | −45 | −1 | 2.35 | 0.25 | 2.01 (0.072) | −4.31 (<0.001) |
| R | Superior Occipital Gyrus | 25 | −84 | 15 | 2.47 | 0.22 | 1.80 (0.064) | −4.29 (<0.001) |
| L | Middle Occipital Gyrus | −13 | −98 | 0 | 2.55 | 0.18 | 2.44 (0.001) | −1.59 (0.032) |
| L | Cuneus | −7 | −82 | 15 | 2.52 | 0.13 | 1.40 (0.075) | −2.64 (<0.001) |
| L | Cerebellum | −15 | −61 | −21 | 2.52 | 0.18 | 2.82 (0.019) | −3.84 (0.006) |
| L | Inferior Occipital Gyrus | −32 | −81 | −6 | 2.49 | 0.18 | 2.98 (0.001) | −2.16 (0.031) |
| R | Lingual Gyrus | 20 | −53 | −4 | 2.46 | 0.20 | 2.94 (0.004) | −2.18 (0.017) |
| R | Calcarine Gyrus | 10 | −67 | 7 | 2.46 | 0.18 | 1.56 (0.032) | −1.87 (0.002) |
| R | Brainstem | 10 | −29 | −31 | 2.40 | 0.23 | 2.14 (0.019) | −2.89 (0.012) |
| L | Hippocampus | −24 | −29 | −8 | 2.40 | 0.23 | 2.89 (0.021) | −3.84 (0.008) |
| L | Cerebellum | −14 | −62 | −40 | 2.45 | 0.20 | 3.39 (0.014) | −3.88 (0.009) |
| R | Cerebellar Vermis | 7 | −72 | −18 | 2.34 | 0.17 | 3.25 (0.004) | −2.72 (0.053) |
| R | Hippocampus | 20 | −34 | 3 | 2.34 | 0.19 | 4.84 (<0.001) | −1.47 (0.247) |

X, Y, and Z values are the peak coordinates in MNI stereotactic space from the large posterior cortical/cerebellar cluster;

Voxel stats column depicts the mean and standard deviation of the voxelwise statistics for a 6 mm radius sphere centered around the peak;

Extractions column reports the parameter and significance value for the activation moderator × time effect within each treatment arm using extracted individual peak sphere beta values for each participant;

FDR = false discovery rate;

Hem = hemisphere;

L = left;

R = right;

Sig. = significance.

TABLE 6

Whole-Brain Non-Specific Treatment Outcome-Predicting Conflict Regulation (iI-cI) Activation Across Both Sertraline and Placebo.

| Hem. | MNI Atlas Region(s) | # Voxels | X | Y | Z | Voxel Stats FDR Z Mean | SD | Extractions Parameter (Sig.) MDD (Sertraline and Placebo) |
|---|---|---|---|---|---|---|---|---|
| L | Anterior Cingulate Cortex/ Superior Medial Gyrus | 234 | −6 | 44 | 12 | 2.19 | 0.14 | 4.03 (<0.001) |
| L/R | Anterior Cingulate Cortex | 46 | 0 | 32 | 28 | 2.10 | 0.09 | 2.52 (<0.001) |

X, Y, and Z values are cluster peak coordinates in MNI stereotactic space;
Voxel stats column depicts the mean and standard deviation of the voxelwise statistics for each cluster's effect;
Extractions column reports the parameter and significance value for the activation moderator × time effect across both treatment arms (non-specific predictive effect) using extracted individual cluster beta values for each participant;
FDR = false discovery rate;
Hem = hemisphere;
L = left;
R = right;
Sig. = significance.

TABLE 7

Whole-Brain Treatment Outcome-Moderating Conflict Response (inc-con) Activation.

| Hem. | MNI Atlas Region(s) | # Voxels | X | Y | Z | Voxel Stats FDR Z Mean | SD | Extractions Parameter (Sig.) Sertraline | Placebo |
|---|---|---|---|---|---|---|---|---|---|
| L | Inferior Parietal Lobule | 151 | −50 | −38 | 36 | 2.17 | 0.13 | −5.33 (<0.001) | 0.79 (0.264) |
| L | Postcentral Gyrus | 98 | −60 | −12 | 14 | 2.13 | 0.11 | −1.70 (0.031) | 2.05 (<0.001) |
| L | Inferior Frontal Gyrus (Pars Opercularis) | 62 | −60 | 14 | 14 | 2.15 | 0.12 | −1.54 (0.030) | 2.25 (0.001) |
| L | SMA | 49 | −2 | 20 | 66 | 2.14 | 0.12 | −1.52 (0.008) | 2.06 (0.001) |
| L | Putamen | 48 | −28 | 2 | 8 | 2.15 | 0.12 | −1.14 (0.237) | 4.12 (<0.001) |
| R | Inferior Occipital Gyrus | 46 | 40 | −72 | −6 | 2.14 | 0.10 | −1.79 (0.020) | 2.39 (0.003) |
| L | Inferior Frontal Gyrus (Pars Orbitalis) | 44 | −34 | 46 | −16 | 2.16 | 0.13 | −1.72 (0.018) | 1.74 (0.008) |
| L | Fusiform Gyrus | 40 | −24 | −82 | −10 | 2.16 | 0.13 | −1.59 (0.042) | 2.52 (<0.001) |
| L | Middle Frontal Gyrus | 31 | −36 | 42 | 28 | 2.03 | 0.05 | −0.53 (0.328) | 1.59 (0.001) |
| L | Calcarine Gyrus | 29 | 0 | −96 | 2 | 2.09 | 0.10 | −2.11 (0.011) | 1.15 (0.027) |
| R | Calcarine Gyrus | 29 | 12 | −92 | 10 | 2.11 | 0.11 | −1.96 (0.006) | 1.60 (0.004) |
| R | Parahippocampal Gyrus | 21 | 18 | −22 | −18 | 2.16 | 0.12 | −1.89 (0.004) | 1.94 (0.002) |
| L | Middle Frontal Gyrus | 21 | −30 | 46 | 14 | 2.14 | 0.11 | −0.70 (0.350) | 2.65 (<0.001) |
| L | Inferior Parietal Lobule | 20 | −62 | −50 | 36 | 2.07 | 0.08 | −1.56 (0.004) | 1.27 (0.040) |
| L | SMA | 20 | −10 | −2 | 76 | 2.17 | 0.10 | −1.33 (0.021) | 1.51 (0.002) |

X, Y, and Z values are cluster peak coordinates in MNI stereotactic space;
Voxel stats column depicts the mean and standard deviation of the voxelwise statistics for each cluster's effect;
Extractions column reports the parameter and significance value for the activation moderator × time effect within each treatment arm using extracted individual cluster beta values for each participant;
FDR = false discovery rate;
Hem = hemisphere;
L = left;
R = right;
Sig. = significance.

Example 3

Figure 8:
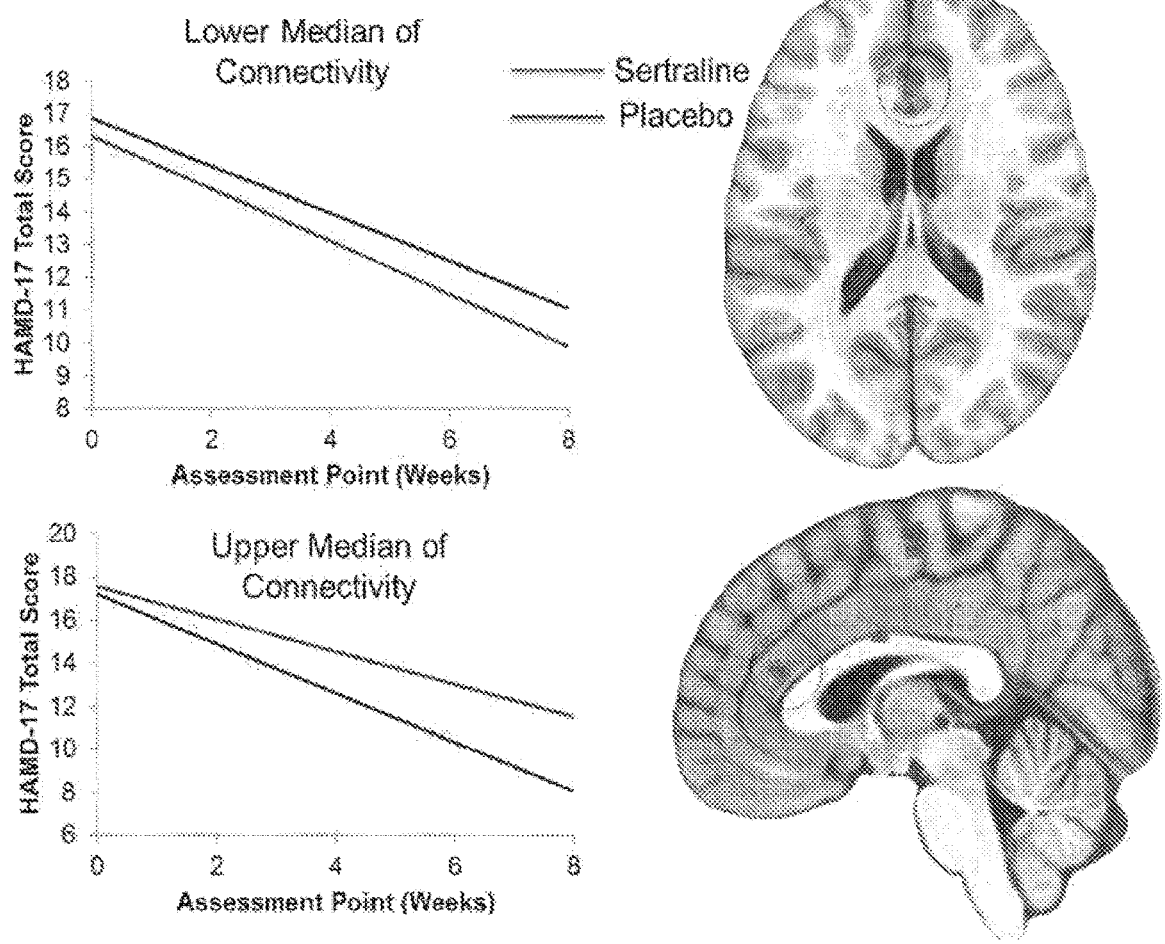
FIG. 8. Shown are treatment-moderating patterns of task related connectivity using psychophysiological interaction analyses. Specifically, these are whole-brain corrected regions showing significant connectivity×group×time interactions using a connectivity seed in the left amygdala. The line plots demonstrate the results of the linear mixed models using a median split for visualization. As can be seen, individuals whose left amygdala PPI connectivity to the dorsal anterior cingulate (circled target region) is below the median value showed a steep decline in symptoms with sertraline treatment compared to placebo (i.e. a clear advantage of the drug in these individuals). By contrast, individuals with above median PPI connectivity failed to show any difference in the symptom change with sertraline versus placebo (i.e. had no advantage of drug over placebo).

Generalized Psychophysiological Interaction Analysis to Assess Task-Dependent Functional Connectivity Context-dependent connectivity analyses were conducted using the generalized PPI toolbox[1]. A "seed" region was defined volumetrically using an anatomical region of interest mask of the left and right amygdala. Each amygdala mask was then deformed from Montereal Neurological Institute standard space into the participant's native anatomical space using the inverse warp parameter determined during spatial normalization of the preprocessing stage. The principal eigenvariate of the seed region time series was extracted from each participant's amygdala seed region in native space and deconvolved with a canonical hemodynamic response function in order to estimate a theoretical "neuronal" time series driving the observed BOLD signal changes. The interaction of the time series of behavioral parameters of interest, i.e. the task conditions utilized in the first-level activation analysis, with the deconvolved "neuronal" time series were calculated for each task condition of interest, thus producing a fully specified statistical model modeling the interaction of each task condition with the observed BOLD time series (a psychophysiological interaction). These psychophysiological interaction time series were then reconvolved with the canonical hemodynamic response function and entered into a first-level analysis along with six motion regressors of no interest. The first-level beta weights for the contrasts of conditions of interest were then calculated on the individual level, and individual-level generalized PPI beta maps were then carried to a second level linear mixed model analysis conducted in R using the fmri$^2$ and nlme$^3$ packages to assess voxelwise task-dependent connectivity moderation effects (as in the activation analyses). See FIG. 8.

REFERENCES

References for Example 2

1. Hasin D S, Sarvet A L, Meyers J L, et al. Epidemiology of Adult DSM-5 Major Depressive Disorder and Its Specifiers in the United States. JAMA Psychiatry 2018.
2. Lopez-Munoz F, Alamo C. Monoaminergic neurotransmission: the history of the discovery of antidepressants from 1950s until today. Curr Pharm Des 2009; 15:1563-86.
3. Moore T J, Mattison D R. Adult Utilization of Psychiatric Drugs and Differences by Sex, Age, and Race. JAMA Intern Med 2017; 177:274-5.
4. Kirsch I. The Emperor's New Drugs: Exploding the Antidepressant Myth: Random House; 2009.
5. Khan A, Brown W A. Antidepressants versus placebo in major depression: an overview. World Psychiatry 2015; 14:294-300.
6. Kirsch I, Deacon B J, Huedo-Medina T B, Scoboria A, Moore T J, Johnson B T. Initial severity and antidepressant benefits: a meta-analysis of data submitted to the Food and Drug Administration. PLoS Med 2008; 5:e45.
7. Fournier J C, DeRubeis R J, Hollon S D, et al. Antidepressant drug effects and depression severity: a patient-level meta-analysis. JAMA 2010; 303:47-53.
8. Cipriani A, Furukawa T A, Salanti G, et al. Comparative efficacy and acceptability of 21 antidepressant drugs for the acute treatment of adults with major depressive disorder: a systematic review and network meta-analysis. Lancet 2018.
9. Drysdale A T, Grosenick L, Downar J, et al. Resting-state connectivity biomarkers define neurophysiological subtypes of depression. Nat Med 2017; 23:28-38.
10. Kraemer H C. Messages for Clinicians: Moderators and Mediators of Treatment Outcome in Randomized Clinical Trials. Am J Psychiatry 2016; 173:672-9.
11. Etkin A, Buchel C, Gross J J. The neural bases of emotion regulation. Nat Rev Neurosci 2015; 16:693-700.
12. Gross J J. Handbook of Emotion Regulation. New York, NY: Guilford Press; 2014.
13. Gyurak A, Gross J J, Etkin A. Explicit and implicit emotion regulation: a dual-process framework. Cogn Emot 2011; 25:400-12.
14. Etkin A, Schatzberg A F. Common abnormalities and disorder-specific compensation during implicit regulation of emotional processing in generalized anxiety and major depressive disorders. Am J Psychiatry 2011; 168:968-78.
15. Xue S, Wang S, Kong X, Qiu J. Abnormal Neural Basis of Emotional Conflict Control in Treatment-Resistant Depression. Clin EEG Neurosci 2017; 48:103-10.
16. Xu M, Xu G, Yang Y. Neural Systems Underlying Emotional and Non-emotional Interference Processing: An ALE Meta-Analysis of Functional Neuroimaging Studies. Front Behav Neurosci 2016; 10:220.
17. Egner T, Etkin A, Gale S, Hirsch J. Dissociable neural systems resolve conflict from emotional versus nonemotional distracters. Cereb Cortex 2008; 18:1475-84.
18. Etkin A, Egner T, Peraza D M, Kandel E R, Hirsch J. Resolving emotional conflict: a role for the rostral anterior cingulate cortex in modulating activity in the amygdala. Neuron 2006; 51:871-82.
19. Maier M E, di Pellegrino G. Impaired conflict adaptation in an emotional task context following rostral anterior cingulate cortex lesions in humans. J Cogn Neurosci 2012; 24:2070-9.
20. Gyurak A, Patenaude B, Korgaonkar M S, Grieve S M, Williams L M, Etkin A. Frontoparietal Activation During Response Inhibition Predicts Remission to Antidepressants in Patients With Major Depression. Biol Psychiatry 2016; 79:274-81.
21. Williams L M, Korgaonkar M S, Song Y C, et al. Amygdala Reactivity to Emotional Faces in the Prediction of General and Medication-Specific Responses to Antidepressant Treatment in the Randomized iSPOT-D Trial. Neuropsychopharmacology 2015; 40:2398-408.
22. Etkin A, Patenaude B, Song Y J, et al. A cognitive-emotional biomarker for predicting remission with antidepressant medications: a report from the iSPOT-D trial. Neuropsychopharmacology 2015; 40:1332-42.
23. Langenecker S A, Kennedy S E, Guidotti L M, et al. Frontal and limbic activation during inhibitory control predicts treatment response in major depressive disorder. Biol Psychiatry 2007; 62:1272-80.
24. Trivedi M H, McGrath P J, Fava M, et al. Establishing moderators and biosignatures of antidepressant response in clinical care (EMBARC): Rationale and design. J Psychiatr Res 2016; 78:11-23.
25. Hamilton M. A rating scale for depression. Journal of neurology, neurosurgery, and psychiatry 1960; 23:56.
26. Pizzagalli D, Webb C A, Dillon D G, et al. The incremental predictive validity of rostral anterior cingulate cortex activity in relation to symptom improvement in depression: A randomized clinical trial. JAMA Psychiatry in press.
27. Rush A J, Trivedi M H, Ibrahim H M, et al. The 16-Item Quick Inventory of Depressive Symptomatology (QIDS), clinician rating (QIDS-C), and self-report (QIDS-SR): a psychometric evaluation in patients with chronic major depression. Biol Psychiatry 2003; 54:573-83.
28. Wardenaar K J, van Veen T, Giltay E J, de Beurs E, Penninx B W, Zitman F G. Development and validation of a 30-item short adaptation of the Mood and Anxiety Symptoms Questionnaire (MASA). Psychiatry Res 2010; 179: 101-6.
29. Marquand A F, Wolfers T, Mennes M, Buitelaar J, Beckmann C F. Beyond Lumping and Splitting: A Review of Computational Approaches for Stratifying Psychiatric Disorders. Biol Psychiatry Cogn Neurosci Neuroimaging 2016; 1:433-47.
30. Clayson P E, Larson M J. Adaptation to emotional conflict: evidence from a novel face emotion paradigm. PLoS One 2013; 8:e75776.
31. Tang D, Hu L, Chen A, Clayson P E, Larson M J. The neural oscillations of conflict adaptation in the human frontal region adaptation to emotional conflict: evidence from a novel face emotion paradigm. Biol Psychol 2013; 93:364-72.
32. Larson M J, Clawson A, Clayson P E, Baldwin S A. Cognitive conflict adaptation in generalized anxiety disorder. Biol Psychol 2013; 94:408-18.
33. Suzuki K, Shinoda H. Transition from reactive control to proactive control across conflict adaptation: An sLORETA study. Brain Cogn 2015; 100:7-14.
34. Voigt J, Carpenter L, Leuchter A. Cost effectiveness analysis comparing repetitive transcranial magnetic stimulation to antidepressant medications after a first treatment failure for major depressive disorder in newly diagnosed patients—A lifetime analysis. PLoS One 2017; 12:e0186950.

35. Nguyen K H, Gordon L G. Cost-Effectiveness of Repetitive Transcranial Magnetic Stimulation versus Antidepressant Therapy for Treatment-Resistant Depression. Value Health 2015; 18:597-604.

36. O'Reardon J P, Solvason H B, Janicak P G, et al. Efficacy and safety of transcranial magnetic stimulation in the acute treatment of major depression: a multisite randomized controlled trial. Biol Psychiatry 2007; 62:1208-16.

37. George M S, Lisanby S H, Avery D, et al. Daily left prefrontal transcranial magnetic stimulation therapy for major depressive disorder: a sham-controlled randomized trial. Arch Gen Psychiatry 2010; 67:507-16.

38. Pescosolido B A, Martin J K, Long J S, Medina T R, Phelan J C, Link B G. "A disease like any other"? A decade of change in public reactions to schizophrenia, depression, and alcohol dependence. Am J Psychiatry 2010; 167:1321-30.

39. Fonzo G A, Goodkind M S, Oathes D J, et al. PTSD Psychotherapy Outcome Predicted by Brain Activation During Emotional Reactivity and Regulation. Am J Psychiatry 2017; 174:1163-74.

40. Paez J G, Janne P A, Lee J C, et al. EGFR mutations in lung cancer: correlation with clinical response to gefitinib therapy. Science 2004; 304:1497-500.

41. Lynch T J, Bell D W, Sordella R, et al. Activating mutations in the epidermal growth factor receptor underlying responsiveness of non-small-cell lung cancer to gefitinib. N Engl J Med 2004; 350:2129-39.

42. Petty R D, Dahle-Smith A, Stevenson D A J, et al. Gefitinib and EGFR Gene Copy Number Aberrations in Esophageal Cancer. J Clin Oncol 2017; 35:2279-87.

43. Etkin A, Prater K E, Hoeft F, Menon V, Schatzberg A F. Failure of anterior cingulate activation and connectivity with the amygdala during implicit regulation of emotional processing in generalized anxiety disorder. Am J Psychiatry 2010; 167:545-54.

44. Korb A S, Hunter A M, Cook I A, Leuchter A F. Rostral anterior cingulate cortex theta current density and response to antidepressants and placebo in major depression. Clin Neurophysiol 2009; 120:1313-9.

45. Kerns J G, Cohen J D, MacDonald A W, 3rd, Cho R Y, Stenger V A, Carter C S. Anterior cingulate conflict monitoring and adjustments in control. Science 2004; 303: 1023-6.

46. Insel T R, Cuthbert B N. Medicine. Brain disorders? Precisely. Science 2015; 348:499-500.

Referenced for Example 2 Additional Methods

1. First M, Spitzer R, Gibbon M, William J. Structured Clinical Interview fpr DSM-IV-TR Axis 1 disorders, Research Version, Patient Edition (SCID-UP) New York, NY: New York State Psychiatric Institute, Biometric research; 2002. 73 Maxwell, M. Bethesda, MD 1992.

2. Trivedi M H, McGrath P J, Fava M, et al. Establishing moderators and biosignatures of antidepressant response in clinical care (EMBARC): Rationale and design. J Psychiatr Res 2016; 78:11-23.

3. Egner T, Etkin A, Gale S, Hirsch J. Dissociable neural systems resolve conflict from emotional versus nonemotional distracters. Cereb Cortex 2008; 18:1475-84.

4. Etkin A, Egner T, Peraza D M, Kandel E R, Hirsch J. Resolving emotional conflict: a role for the rostral anterior cingulate cortex in modulating activity in the amygdala. Neuron 2006; 51:871-82.

5. Ekman P, Friesen W V. Pictures of Facial Affect. Palo Alto, CA: Consulting Psychologists; 1976.

6. Jenkinson M, Beckmann C F, Behrens T E, Woolrich M W, Smith S M. FSL. Neuroimage 2012; 62:782-90.

7. Smith S M, Jenkinson M, Woolrich M W, et al. Advances in functional and structural MR image analysis and implementation as FSL. Neuroimage 2004; 23 Suppl 1:S208-19.

8. Friston K J, Holmes A P, Worsley K J, Poline J B, Frith C D, Frackowiak R S. Statistical parametric maps in functional imaging: a general linear approach. Hum Brain Mapp 1995; 2:189-210.

9. Fonzo G A, Goodkind M S, Oathes D J, et al. PTSD Psychotherapy Outcome Predicted by Brain Activation During Emotional Reactivity and Regulation. Am J Psychiatry 2017; 174:1163-74.

10. Fonzo G A, Goodkind M S, Oathes D J, et al. Selective Effects of Psychotherapy on Frontopolar Cortical Function in PTSD. Am J Psychiatry 2017; 174:1175-84.

11. IBM. IBM SPSS Statistics for Macintosh, Version 21.0. Armonk, NY: IBM Corp; 2012.

12. Team R C. R: A language and environment for statistical computing. 3.2.3 ed. Vienna, Austria: R Foundation for Statistical Computing; 2015.

13. Tabelow K, Polzehl J. Statistical Parametric Maps for Functional MRI Experiments in R: The Package fmri. 2011 2011; 44:21.

14. Pinheiro J, Bates D, DebRoy S, Sarkar D, Team. R C. nlme: Linear and Nonlinear Mixed Effects Models. 2015.

15. Tibshirani R. Regression shrinkage and selection via the Lasso. J Roy Stat Soc B Met 1996; 58:267-88.

16. Cawley G C, Talbot N L. Preventing over-fitting during model selection via Bayesian regularisation of the hyper-parameters. Journal of Machine Learning Research 2007; 8:841-61.

17. Tipping M E. Sparse Bayesian Learning and the Relevance Vector Machine. Journal of Machine Learning Research 2001; 1:211-44.

18. Wipf D P, Rao B D. Sparse Bayesian Learning for Basis Selection. IEEE Transactions on Signal Processing 2004; 52:2153-64.

19. Zhang Y, Zhou G, Jin J, Zhao Q, Wang X, Cichocki A. Sparse Bayesian classification of EEG for brain-computer interface. IEEE Transactions on Neural Networks and Learning Systems 2016; 27:2256-67.

20. Cawley G C, Talbot N L. Gene selection in cancer classification using sparse logistic regression with Bayesian regularization. Bioinformatics 2006; 22:2348-55.

21. Li Y, Campbell C, Tipping M. Bayesian automatic relevance determination algorithms for classifying gene expression data. Bioinformatics 2002; 18:1332-9.

22. van Buuren S, Groothuis-Oudshoorn K. mice: Multivariate Imputation by Chained Equations in R. 2011 2011; 45:67.

23. Schaefer A, Kong R, Gordon E M, et al. Local-Global Parcellation of the Human Cerebral Cortex from Intrinsic Functional Connectivity Mill. Cereb Cortex 2017: 1-20.

24. Choi E Y, Yeo B T, Buckner R L. The organization of the human striatum estimated by intrinsic functional connectivity. J Neurophysiol 2012; 108:2242-63.

25. Buckner R L, Krienen F M, Castellanos A, Diaz J C, Yeo B T. The organization of the human cerebellum estimated by intrinsic functional connectivity. J Neurophysiol 2011; 106:2322-45.

26. Patenaude B, Smith S M, Kennedy D N, Jenkinson M. A Bayesian model of shape and appearance for subcortical brain segmentation. Neuroimage 2011; 56:907-22.

27. Chen A C, Etkin A. Hippocampal network connectivity and activation differentiates post-traumatic stress disorder from generalized anxiety disorder. Neuropsychopharmacology: official publication of the American College of Neuropsychopharmacology 2013; 38:1889-98.

28. Behrens T E, Johansen-Berg H, Woolrich M W, et al. Non-invasive mapping of connections between human thalamus and cortex using diffusion imaging. Nat Neurosci 2003; 6:750-7.

References for Example 3

1. McLaren D G, Ries M L, Xu G, Johnson S C. A generalized form of context-dependent psychophysiological interactions (gPPI): a comparison to standard approaches. Neuroimage 2012; 61:1277-86.

2. Tabelow K, Polzehl J. Statistical Parametric Maps for Functional MRI Experiments in R: The Package fmri. 2011 2011; 44:21.

3. Pinheiro J, Bates D, DebRoy S, Sarkar D, Team. R C. nlme: Linear and Nonlinear Mixed Effects Models. 2015.

What is claimed is:

1. A method of identifying a subject suffering from depression that is likely to respond to treatment with an antidepressant, said method comprising:
(a) administering a first incongruent trial followed by a second incongruent trial to said subject, and measuring a first brain activity level in a plurality of brain regions of said subject in response to said second incongruent trial, wherein said first and second incongruent trials form part of an emotional conflict task;
(b) administering a congruent trial followed by a third incongruent trial to said subject, and measuring a second brain activity level in said plurality of brain regions of said subject in response to said third incongruent trial, wherein said congruent and third incongruent trials form part of said emotional conflict task;
(c) quantifying a difference between said first brain activity level in each of said plurality of brain regions and said second brain activity level in each of said plurality of brain regions, respectively; and
(d) identifying whether said subject will respond to treatment with an antidepressant by at least applying to each of said differences a machine learning model;
wherein the plurality of brain regions comprises two or more of a frontopolar cortex, a lateral prefrontal cortex, a dorsal anterior cingulate cortex, and an anterior insula.

2. The method of claim 1, wherein said first brain activity level and said second brain activity level are measured via functional magnetic resonance imaging (fMRI), electroencephalography (EEG), functional near-infrared spectroscopy (fNIRS), or magnetoencephalography (MEG).

3. The method of claim 1, wherein said antidepressant is a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, or an over-the-counter antidepressant.

4. The method of claim 3, wherein said SSRI is sertraline.

5. The method of claim 1, wherein said machine learning model comprises a neural network, a regression model, an instance-based model, a regularization model, a decision tree, a Bayesian model, a clustering model, an associative model, a deep learning model, a dimensionality reduction model, and/or an ensemble model.

6. The method of claim 5, wherein said Bayesian model is a Sparse Bayesian Learning model.

7. The method of claim 1, wherein said machine learning model is trained to identify, based on said differences, whether said subject will respond to treatment with an antidepressant.

8. The method of claim 1, further comprising training, based at least on training data, said machine learning model, said training data comprising a plurality of differences, and said machine learning model being trained to identify differences indicative of whether said subject will respond to treatment with an antidepressant.

9. A method of detecting a brain activity level in brain regions of a subject suffering from depression, said method comprising:
(a) administering a first incongruent trial followed by a second incongruent trial to said subject, and measuring a first brain activity level in a brain region of said subject in response to said second incongruent trial, wherein said first and second incongruent trials form part of an emotional conflict task;
(b) administering a congruent trial followed by a third incongruent trial to said subject, and measuring a second brain activity level in said brain region of said subject in response to said third incongruent trial, wherein said congruent and third incongruent trials form part of said emotional conflict task; and
(c) quantifying a difference between said first brain activity level in said brain region and said second brain activity level in said brain region;
wherein steps (a), (b), and (c) are performed in a first brain region, a second brain region, a third brain region, and a fourth brain region;
wherein each of said first brain region, said second brain region, said third brain region, and said fourth brain region is different, wherein said first brain region is selected from the group consisting of a frontopolar cortex, a dorsal anterior cingulate cortex, and an anterior insula, wherein the second brain region, the third brain region, and the fourth brain region are independently selected from the frontopolar cortex, a lateral prefrontal cortex, the dorsal anterior cingulate cortex, and the anterior insula.

10. The method of claim 9, wherein said first brain activity level and said second brain activity are measured via functional magnetic resonance imaging (fMRI), electroencephalography (EEG), functional near-infrared spectroscopy (fNIRS), or magnetoencephalography (MEG).

11. The method of claim 9, further comprising determining whether said subject is an antidepressant responsive subject, wherein said second brain activity level in said first brain region of said subject being greater than said first brain activity level in said first brain region of said subject is indicative of said subject being an antidepressant responsive subject.

12. The method of claim 11, wherein said antidepressant is a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, or an over-the-counter antidepressant.

13. The method of claim 12, wherein said SSRI is sertraline.

14. The method of claim 1, wherein the plurality of brain regions comprises three or more of the frontopolar cortex, the lateral prefrontal cortex, the dorsal anterior cingulate cortex, and the anterior insula.

15. The method of claim 14, wherein the plurality of brain regions comprises each of the frontopolar cortex, the lateral prefrontal cortex, the dorsal anterior cingulate cortex, and the anterior insula.

* * * * *